US00RE40861E

(19) United States
(12) Reissued Patent
Giannessi et al.

(10) Patent Number: US RE40,861 E
(45) Date of Reissued Patent: *Jul. 21, 2009

(54) COMPOUNDS HAVING REVERSIBLE INHIBITING ACTIVITY OF CARNITINE PALMITOYL-TRANSFERASE

(75) Inventors: Fabio Giannessi, Rome (IT); Mauro Marzi, Rome (IT); Patrizia Minetti, Rome (IT); Francesco De Angelis, Rome (IT); Maria O. Tinti, Rome (IT); Piero Chiodi, Rome (IT); Arduino Arduini, Rome (IT)

(73) Assignee: Sigma-Tau Industrie Farmaceutiche Reunite S.p.A., Rome (IT)

( * ) Notice: This patent is subject to a terminal disclaimer.

(21) Appl. No.: 11/606,322

(22) Filed: Nov. 30, 2006

Related U.S. Patent Documents

Reissue of:
(64) Patent No.: 6,369,073
Issued: Apr. 9, 2002
Appl. No.: 09/677,328
Filed: Oct. 2, 2000

U.S. Applications:
(63) Continuation of application No. PCT/IT99/000126, filed on May 11, 1999.

(30) Foreign Application Priority Data

May 15, 1998 (IT) ..... MI98A1075

(51) Int. Cl.
*A61K 31/46* (2006.01)
*C07D 453/02* (2006.01)

(52) U.S. Cl. ..... 514/305; 546/133; 546/22; 548/252; 564/17; 564/32; 564/47; 564/63; 564/79; 514/357; 514/381; 514/476; 514/588; 514/600

(58) Field of Classification Search ..... 514/305, 514/357, 381, 476, 588, 600; 546/133, 22; 548/252; 564/17, 32, 47; 560/155, 179
See application file for complete search history.

(56) References Cited

U.S. PATENT DOCUMENTS

| | | | | |
|---|---|---|---|---|
| 3,810,994 | A | 5/1974 | Wiegand | |
| 4,599,232 | A | 7/1986 | Bertelli | |
| 4,784,992 | A | 11/1988 | Reiner | |
| 5,196,418 | A | 3/1993 | Gandour et al. | |
| 6,528,684 | B1 * | 3/2003 | Giannessi et al. | 562/561 |
| 6,822,115 | B2 * | 11/2004 | Giannessi et al. | 562/561 |
| 6,953,865 | B2 * | 10/2005 | Piccoloi et al. | 562/561 |

FOREIGN PATENT DOCUMENTS

| | | | |
|---|---|---|---|
| EP | 0 127 098 | | 12/1984 |
| EP | 0 574 355 | A | 12/1993 |
| EP | 0 591 857 | A | 4/1994 |
| EP | 1 484 313 | A1 | 12/2004 |
| WO | WO 85 04396 | A | 10/1985 |
| WO | WO 93 25197 | A | 12/1993 |
| WO | WO 98 00389 | A | 1/1998 |

OTHER PUBLICATIONS

Zhi–Heng Huang et al, "Analysis of Acylcarnitines as Their N–Demethylated Ester . . . ", Analytical Biochemistry, vol. 199, No. 1, Nov. 15, 1991, pp. 98–105; XP002115164.

Anderson Current Pharmaceutical Design, 1998, 4, 1–15 "Carnitine Palmitoyltransferase: A Viable Target for the Treatment of NIDDM?".

Shinagawa et al J. Med. Chem., 1987, 30, 1458–1463 "Chemistry and Inhibitory Activity of Long Chain Fatty Acid Oxidation of Emeriamine and Its Analogues".

Nutrition Reviews, vol. 48, No. 6, Jun. 1990 "Aminocarnitine and related compounds as inhibitors of carnitine transferases: Physiologic Implications".

Kanamaru et al Novel Microbial Products for Medicine and Agriculture, 135–144 "Emeriamine: a new inhbitor of long chain fatty acid oxidation and its antidiabetic activity".

Anderson et al J. Med. Chem., 1995, 38, 3448–3450 Antidiabetic Agents: A New Class of Reversible Carnitine Palmitoyltranserase I Inhibitors.

Nagen et al ACS 212 mtg. Aug. 25–29, 1996, Abst Medi 133 "Synthesis and Biological Activity of A chiral and Reversible Inhibitors of Carnitine Palitoyl transferase I".

Fraser et al ACS, 214 mtg. Sep. 7–11, 1997 Abst. Medi 207 "A series of monothiophosphate carnitine analogs, potent carnitine, palmitoyltrnsferase I inhibitors".

Deems et al Am. J. Physiol. vol. 274, Issue 2, R524–528, Feb. 1998 "Hypoglycemic effects of a novel fatty acid oxidation inhibitor in rats and monkeys".

Gandour et al Archives of Biochemistry and Biophysics, vol. 267, No. 2, Dec, 515–520 Hemipalmitoylcarnitinium, a Strong Competitive Inhibitor of Purified Hepatic Carnitine Palmitoyltransferase.

Gandour et al J. Org. Chem., 1992, 57, 3426–3431 "Synthesis, Structures and Enzymatic Evaluations of Hemiacrylcarnitiniums, a New Class of Carnitine Acyltransferase Inhibitors".

*Primary Examiner*—Charanjit S Aulakh
(74) *Attorney, Agent, or Firm*—Nixon & Vanderhye P.C.

(57) ABSTRACT

Compounds of formula (I)

wherein the groups are as defined in the description are disclosed.

The compounds of formula (I) are endowed with reversible inhibiting activity of carnitine palmitoyl-transferase and are useful in the preparation of medicaments useful in the pathologies related to a hyperactivity of carnitine palmitoyl-transferase, such as hyperglycemia, diabetes and pathologies related thereto, heart failure, ischemia.

14 Claims, 5 Drawing Sheets

OTHER PUBLICATIONS

Gandour et al J. Med. Chem., 1993, 36, 237–242 "Hemipalmitoylcarnitium Strongly Inhibits Carnitine Palmitoyltransferase–I in Intact Mitochondria".

Selby et al TIPS, Dec. 1989, vol. 10, 495–500 "Substituted 2–oxiranecaboxylic acids: a new group of candidate hypoglycaemic drugs".

Ratheiser et al Metabolism, vol. 40 No. 11 (Nov. 1991), 1185–1190 Inhibition of Etomoxir of Carnitine Palmitoyl–transferase I Reduces Hepatic Glucose Production and Plasma Lipids in Non–Insulsin–Dependent Diabetes Mellitus.

* cited by examiner $R_4$= a)$-(CH_2)_7CH_3$
b)$-(CH_2)_8CH_3$

A) base
B) IRA 402/$OH^-$form $R_4$ = a)$-(CH_2)_7CH_3$
b)$-(CH_2)_{13}CH_3$

A) $R_4OH$, $SOCl_2$
B) $Et_3SiH$, $BF_3.Et_2O$
C) $NaN_3$
D) Pd/C $H_2$, HCHO
E) $CH_3I$
F) IRA 402 $OH^-$

A) NaOH 4N, MeOH, 16h, t.a

B) $H_2NCH_2H_2CN$, DMF, TEA, DEPC

C) THF, $Ph_3P$

D) $(BOC)_2O$, NaOH 1N

E) THF, $PH_3P$, DEAD, $Et_3SiN_3$

F) HCl 3N, NaOH 1N $R_4$= a)$-(CH_2)_7CH_3$
b)$-(CH_2)_{13}CH_3$

A) 1)BuLI 2)$BF_3 \cdot Et_2O$
B) $R_4OCOCl$, Base
C) $R_4N{=}C{=}O$, $BF_3 \cdot Et_2O$
D) Quinuclidine F) Trimethylamine
H) Pyridine
E=G) $H_2$,Pd/C

COMPOUNDS HAVING REVERSIBLE INHIBITING ACTIVITY OF CARNITINE PALMITOYL-TRANSFERASE

Matter enclosed in heavy brackets [ ] appears in the original patent but forms no part of this reissue specification; matter printed in italics indicates the additions made by reissue.

This application is a continuation of PCT/IT00126 filed May 11, 1999.

The present invention relates to compounds having inhibiting activity against carnitine palmitoyl transferase. The present invention relates also to pharmaceutical compositions containing at least one of these compounds active ingredients and to the use of said compounds in the preparation of medicaments useful in the treatment of pathologies related to a hyperactivity of carnitine palmitoyl-transferase, in particular hyperglycaemic states, such as diabetes and related pathologies and of congestive heart failure.

BACKGROUND OF THE INVENTION

To date, hypoglycaemic therapy is based on the use of drugs having different mechanism of action (Arch. Intern. Med., 1997, 157, 1802–1817).

Insulin and its analogues represent the most used therapy, recurring to the direct hypoglycaemic action of this hormone.

Other compounds act indirectly by stimulating insulin release (sulphonylureas). A different target of hypoglycaemic drugs is represented by the reduction of glucose intestinal absorption through the inhibition of intestinal glucosidases, or by reducing insulin resistance.

Hyperglycaemia is also treated with gluconeogenesis inhibitors, such as biguanides.

Some words have also stressed out the relationship between gluconeogenesis and fatty acid oxidation.

The membrane bound long-chain acylcarnitine transferases, also known as carnitine palmitoyltransferase (CPT), are widely represented in organs and subcellular organelles (Bieber, L. L. 1988 Ann. Rev. Biochem. 57: 261–83). The well-established role of this category of enzymes is the transport of activated long-chain fatty acids through mitochondrial membranes. In this context, the outer mitochondrial membrane CIT I catalyzes the formation of long-chain acylcarnitines that are transported across the mitochondrial membrane by a specific carrier, and reconverted into long-chain acyl-coenzyme A esters by CPT II, which resides in the inner mitochondrial membrane. Long-chain acyl-CoAs are then oxidised to acetyl-coenzyme A, which activates a key gluconeogenetic enzyme: pyruvate carboxylase.

Other works report that diabetic patients have high blood levels of fatty acids, whose liver oxidative fate gives rise to an increase of acetyl-coenzyme A, ATP and NADH. High availability of these compounds maximally stimulates gluconeogenesis, which is in part responsible of the elevated glucose blood levels in diabetic patients. CPT inhibition indirectly reduces the extent of liver gluconeogenesis, and hence blood glucose levels.

CPT inhibitors have been disclosed in J. Med. Chem., 1995, 38(18), 3448–50 and in the corresponding European patent application EP 0574 355 as potential derivatives with hypoglycaemic activity.

Aminocarnitines N-acylated with —COR residue, wherein R is an aliphatic residue with 1 to 19 carbon atoms are disclosed in WO85/04396 useful for investigating the role of transferases in the body, in particular the specificity of carnitine acyltransferase.

Emeriamine and its analogues are disclosed in EP 0 127 098 and J.Med. Chem. 1987, 30, 1458–1463.

Notwithstanding the mechanism of activity above outlined, to date, drugs inhibiting CPT capable to effectively counteract hyperglycaemia do not exist. For some products, such as tetradecyl glycidic acid, or etomoxir, myocardial hypertrophy have been evidenced as side effects (Life Sci., 1989, 44, 1897–1906).

None of the therapies presently used in clinic is fully satisfying, in particular due to the onset of unwanted side effects, such as severe hyperglycaemia, allergic phenomena, oedema, diarrhoea, intestinal disturbances, kidney toxicity, etc.

The necessity to obtain alternative effective therapies for hyperglycaemia still remains.

[ABSTRACT OF THE INVENTION]

*BRIEF DESCRIPTION OF THE INVENTION*

Figure 1:
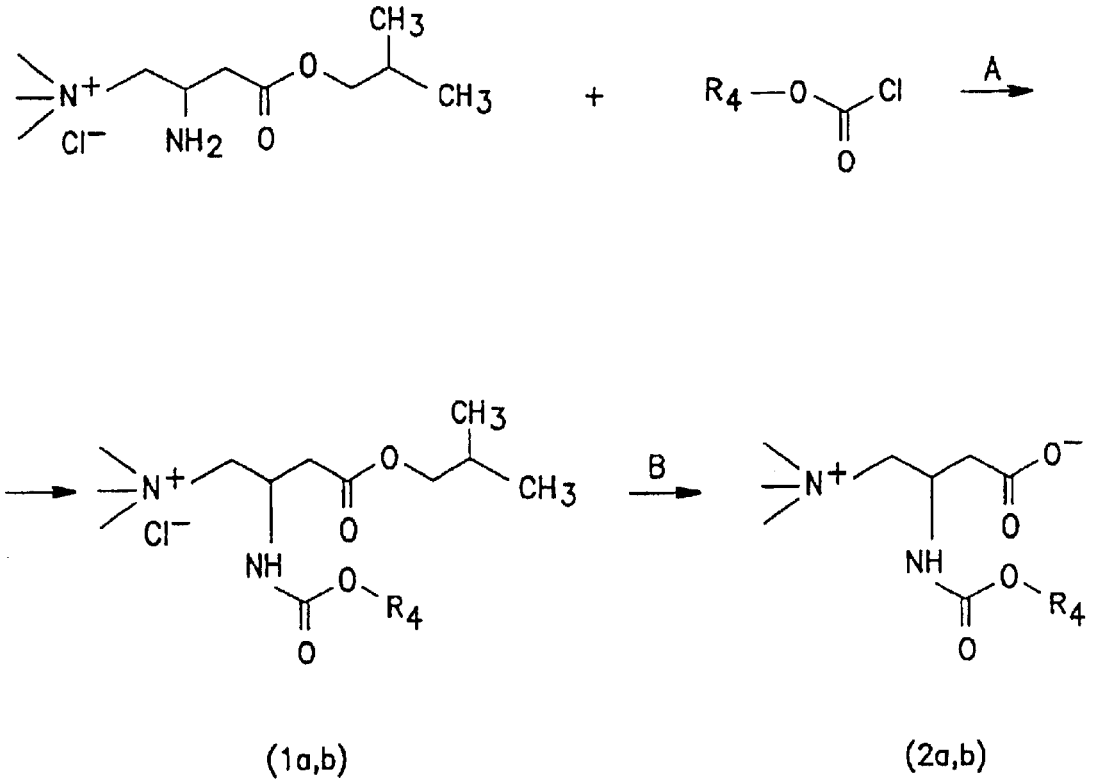
*FIG. 1 is a flow chart illustrating examples 6 and 7;*

It has now surprisingly been found that compounds of general formula (I):

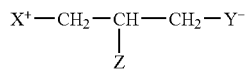

wherein: $X^+$ is selected from the group consisting of $N^+(R_1,R_2,R_3)$ and $P^+(R_1,R_2,R_3)$, wherein $(R_1,R_2,R_3)$, being the same or different, are selected in the group consisting of hydrogen and $C_1$–$C_9$ straight or branched alkyl groups, —CH═NH($NH_2$), —$NH_2$, —OH; or two or more $R_1$, $R_2$ and $R_3$ together with the nitrogen atom, which they are linked to, form a saturated or unsaturated, monocyclic or bicyclic heterocyclic system; with the proviso that at least one of the $R_1$, $R_2$ and $R_3$ is different from hydrogen;

Z is selected from

—$OR_4$,
—$OCOOR_4$,
—$OCONHR_4$,
—$OCSNHR_4$,
—$OCSOR_4$,
—$NHR_4$,
—$NHCOR_4$,
—$NHCSR_4$,
—$NHCOOR_4$,
—$NHCSOR_4$,
—$NHCONHR_4$,
—$NHCSNHR_4$,
—$NHSOR_4$,
—$NHSONHR_4$,
—$NHSO_2R_4$,
—$NHSO_2NHR_4$,

—$SR_4$, wherein —$R_4$ is a $C_1$–$C_{20}$ saturated or unsaturated, straight or branched alkyl group, optionally substituted with a $A_1$ group, wherein $A_1$ is selected from the group consisting of halogen atom, $C_6$–$C_{14}$ aryl, heteroaryl, aryloxy or heteroaryloxy group, said aryl, heteroaryl, aryloxy or heteroaryloxy groups being optionally substituted with one or more $C_1$–$C_{20}$ saturated or unsaturated, straight or branched alkyl or alkoxy group and/or halogen atom;

$Y^-$ is selected from the group consisting of —COO—, $PO_3H^-$, —$OPO_3H^-$, tetrazolate-5-yl;

with the proviso that when Z is —$NHCOR_4$, $X^+$ is trimethylammonium, Y is —COO—, then $R_4$ is $C_{20}$ alkyl;

with the proviso that when Z is —$NHSO_2R_4$, $X^+$ is trimethylammonium and $Y^-$ is —COO—, then $R_4$ is not tolyl;

with the proviso that when Z is —$NHR_4$, $X^+$ is trimethylammonium and $Y^-$ is —COO—, then $R_4$ is not $C_1$–$C_6$ alkyl.

The present invention further comprises the use of the compounds of the above-mentioned formula (I) as active ingredients for medicaments, in particular for medicaments useful for the treatment of pathologies related to a hyperactivity of carnitine palmitoyl carnitine, such as and in particular hyperglycemic states, diabetes and related pathologies, congestive heart failure and dilatative cardiopathy.

The present invention comprises pharmaceutical compositions containing compounds of formula (I) as active ingredients, in admixture with pharmaceutically acceptable vehicles and excipients.

The present invention comprises also processes for the preparation of compounds of formula (I).

DETAILED DESCRIPTION OF THE INVENTION

Within the scope of the present invention, as examples of $C_1$–$C_{20}$ linear or branched alkyl group, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl and their possible isomers are meant, such as for example isopropyl, isobutyl, tert-butyl.

Examples of $C_1$–$C_{20}$ linear or branched alkenyl group are methylene, ethylidene, vinyl, allyl, [propargyl, butylene, pentylene] *propenyl, butenyl, pentenyl*, wherein the carbon-carbon double bond, optionally in the presence of other carbon-carbon unsaturations, can be situated in the different possible positions of the alkyl chain, which can also be branched within the allowed isomery.

Examples of ($C_6$–$C_{14}$) aryl group are phenyl, 1- or 2-naphthyl, anthryl, optionally substituted as shown in the general definitions above-mentioned.

Examples of heterocyclic groups thienyl, quinolyl, pyridyl, N-methylpiperidinyl, 5-tetrazolyl, optionally substituted as shown in the general definitions above-mentioned.

As halogen atom it is intended fluorine, chlorine, bromine, iodine.

The compounds of formula (I) can be also in the form of inner salts.

A first group of preferred compounds comprises the compounds of formula (I) wherein $N^+$ ($R_1$,$R_2$,$R_3$) is trimethyl ammonium.

A second group of preferred compounds comprises the compounds of formula (I) wherein two or more $R_1$, $R_2$ and $R_3$, together with the nitrogen atom, which they are linked to, form a saturated or unsaturated, monocyclic or bicyclic heterocyclic system; for example morpholinium, pyridinium, pyrrolidinium, quinolinium, quinuclidinium.

A third group of preferred compounds comprises the compounds of formula (I) wherein $R_1$ and $R_2$ are hydrogen and $R_3$ is selected from the group consisting of —CH═NH ($NH_2$), —$NH_2$ and —OH.

Within the different embodiments of the present invention, the $R_4$ group is preferably a $C_7$–$C_{20}$ saturated or unsaturated, straight or branched alkyl group. In fact, it has been observed the length of the alkyl chain $R_4$ significantly increases the selectivity against CPT. referred $R_4$ groups are selected from the group consisting of heptyl, octyl, nonyl, decyl, undecyl, dodecyl, tridecyl, tetradecyl, pentadecyl, hexadecyl, heptadecyl, octadecyl, nonadecyl and eicosyl.

Preferred examples of Z group are ureido (—$NHCONHR_4$), and carbamate (—$NHCOOR_4$, —$OCONHR_4$) ones.

In particular, compounds of formula (I) wherein $X^+$, $R_1$, $R_2$, $R_3$, have the above disclosed meanings, Z is ureido (—$NHCONHR_4$) or carbamate (—$NHCOOR_4$, —$OCONHR_4$), $R_4$ is a $C_7$–$C_{20}$, preferably a $C_9$–$C_{18}$ saturated or unsaturated, straight or branched alkyl group, are preferred.

The compounds of formula (I) have an asymmetry center on carbon atom bound to a Z group. For the purposes of the present invention, each compound of formula (I) can exist both as R,S racemic mixture and as separated R/S isomeric form.

The compounds of formula (I) are quaternary ammonium or phosphonium derivatives always containing a $Y^-$ anionic group. Dependently on pH, each compounds of formula (I) can exist indifferently as amphoion (inner salt) or as a compound wherein $Y^-$ is present in the YH form. In such a case, $X^+$ is salified with a pharmacologically acceptable acid. Formula (I) covers all these different possibilities. In case of nitrogen atoms having basic character, the salts with pharmaceutically acceptable acids, both inorganic and organic, such as for example, hydrochloric acid, sulfuric acid, acetic acid, or, in the case of acid group, such as carboxyl, the salts with pharmaceutically acceptable bases, both inorganic and organic, such as for example, alkaline and alkaline-earth hydroxides, ammonium hydroxide, amine, also heterocyclic ones. Examples of pharmaceutically acceptable salts are chloride; bromide; iodide; aspartate; acid aspartate; citrate; acid citrate; tartrate; acid tartrate; phosphate, acid phosphate; fumarate; acid fumarate; glycerophosphate; glucosephosphate; lactate; maleate; acid maleate; mucate; orotate; oxalate; acid oxalate; sulfate; acid sulfate; trichloroacetate; trifluoroacetate; methanesulfonate; pamoate and acid pamoate.

A first group of particularly preferred compounds comprises:

R,S-4-trimethylammonium-3-(nonylcarbamoyl)-aminobutyrate;

R,S-4-quinuclidinium-3-(tetradecyloxycarbonyl)-oxybutyrate;

R,S-4-trimethylammonium-3-(nonylcarbamoyl)-oxybutyrate;

R,S-4-trimethylammonium-3-(nonyloxycarbonyl)-oxybutyric acid chloride;

R,S-4-trimethylphosphonium-3-(nonylcarbamoyl)-oxybutyrate;

R,S-4-trimethylammonium-3-(octyloxycarbonyl)-aminobutyrate;

R,S-4-trimethylammonium-3-(nonyloxycarbonyl)-aminobutyrate;

R,S-4-trimethylammonium-3-octyloxybutyrate;

R,S-4-trimethylammonium-3-tetradecyloxybutyrate;

R,S-1-guanidinium-2-tetradecyloxy-3-(tetrazolate-5-yl)-propane;

R,S-1-trimethylammonium-2-tetradecyloxy-3-(tetrazolate-5-yl)-propane;

R,S-3-quinuclidinium-2-(tetradecyloxycarbonyl)-oxy-1-propanephosphonate monobasic;

R,S-3-trimethylammonium-2-(nonylaminocarbonyl)-oxy-1-propanephosphonate monobasic;

R,S-3-pyridinium-2-(nonylaminocarbonyl)-oxy-1-propanephosphonic acid chloride;

R-4-trimethylammonium-3-(tetradecylcarbamoyl)-aminobutyrate;

R-4-trimethylammonium-3-(undecylcarbamoyl)-aminobutyrate;

R-4-trimethylammonium-3-(heptylcarbamoyl)-aminobutyrate;

R-4-trimethylammonium-3-(nonylthicarbamoyl)-aminobutyrate;

R,S-4-trimethylammonium-3-(nonylthiocarbamoyl)-aminobutyrate;

R-4-trimethylammonium-3-(nonylcarbamoyl)-aminobutyrate;

S-4-trimethylammonium-3-(nonylcarbamoyl)-aminobutyrate;

S-4-trimethylammonium-3-(tetradecylcarbamoyl)-aminobutyrate;

R,S-4-trimethylammonium-3-tetradecylaminobutyrate;

R,S-4-trimethylammonium-3-octylaminobutyrate;

R,S-4-trimethylammonium-3-(decansulfonyl) aminobutyrate;

R,S-4-trimethylammonium-3-(nonylsulfamoyl) aminobutyrate;

S-4-trimethylammonium-3-(dodecansulfonyl) aminobutyrate;

R-4-trimethylammonium-3-(dodecansulfonyl) aminobutyrate;

S-4-trimethylammonium-3-(undecylsulfamoyl) aminobutyrate;

R-4-trimethylammonium-3-(undecylsulfamoyl) aminobutyrate;

R-4-trimethylammonium-3-(dodecylcarbamoyl) aminobutyrate;

R-4-trimethylammonium-3-(10-phenoxydecylcarbamoyl)aminobutyrate;

R-4-trimethylammonium-3-(trans-β-styrenesulfonyl) aminobutyrate.

The compounds of formula (I) can be prepared with reactions that are well known in the state of the art. A process for the preparation of the compounds of claim 1, wherein Z is —$NHR_4$ comprising the reaction of $X^+$—$CH_2$—CH($NH_2$)—$CH_2$—$Y^-$, wherein $X^+$ and $Y^-$ have the same meanings as in claim 1, of the desired structure, optionally protected on the acid $Y^-$ group, with alkane carbaldheydes, wherein the alkyl moiety is a one-term lower homologue of the desired $R_4$, and subsequent reduction.

Generally, the compounds of formula (I), wherein Z is carbonate (—$OCOOR_4$), carbamate (—$OCONHR_4$, —$NHCOOR_4$), thiocarbamate (—$OCSNHR_4$, —$NHCSOR_4$,) or thiocarbonate (—$OCSOR_4$), are obtained by reacting a compound of formula $X^+$—$CH_2$—CH(OH)—$CH_2$—$Y^-$, wherein $X^+$ and $Y^-$ are as above defined, of the desired structure, optionally protected on the acid $Y^-$ group, respectively with alkyl chloroformates, alkyl isocyanates, alkyl isothiocyanates, alkyl thiochloroformates, containing the desired $R_4$ alkyl group.

Compounds of formula (I), wherein Z is amide (—$NHCOR_4$), thioamide (—$NHCSR_4$), carbamate (—$NHCOOR_4$, —$OCONHR_4$), thiocarbamate (—$NHCSOR_4$, —$OCSNHR_4$,), ureido (—$NHCONHR_4$), thioureido (—$NHCSNHR_4$), sulfinamide (—$NHSOR_4$), sulfonamide (—$NHSO_2R_4$), sulfinamoylamino (—$NHSONHR_4$), and sulfamide (—$NHSO_2NHR_4$), are obtained by reacting $X^+$—$CH_2$—CH($NH_2$)—$CH_2$—Y—, wherein $X^+$ and $Y^-$ are as above defined, of the desired structure, optionally protected on the acid $Y^-$ group, respectively with acyl chlorides, thioacyl chlorides, alkyl chloroformates, alkyl thiochloroformates, alkyl isocyanates, alkyl thioisocyanates, alkyl sulfinyl chlorides, alkyl sulfonyl chlorides, $SOCl_2$ and alkyl amines, alkyl sulfamoyl chlorides (or $SO_2Cl_2$ and alkyl amines), containing the desired $R_4$ alkyl group.

Compounds of formula (I), wherein Z is —OR4 or —SR4 are obtained by the reaction of carbonyl compounds of formula Hal-CH2—CO—CH2—COOR', wherein Hal is a halogen atom, preferably chlorine, and R' is the residue of a suitable ester, such as for example a lower alkyl ester (an ethyl or a tert-butyl ester) with respectively alcohols and thiols R4OH or R4SH, wherein R4 is as above defined, to give the respective ketal or thioketal, followed by the transformation of the respective ketal or thioketal into the respective ether or thioether, subsequent substitution of the Hal atom with a nucleophilic group, such as azido, phthalimido, nitro, amino, alkyl amino group, and transformation of the nucleophilic group into the X+ group, wherein X+ is $N^+(R_1, R_2, R_3)$ or, alternatively the Hal atom is substituted with a $(R_1,R_2,R_3)$-substituted phosphine to obtain the compounds of formula (I) wherein $X^+$ is $P^+(R_1,R_2,R_3)$.

Compounds of formula (I), wherein Z is —$NHR_4$ are obtained by reacting $X^+$—$CH_2$—CH($NH_2$)—$CH_2$—$Y^-$, wherein $X^+$ and $Y^-$ have the same meanings as in claim 1, of the desired structure, optionally protected on the acid $Y^-$ group, with alkane carbaldheydes, wherein the alkyl moiety is a one-term lower homologue of $R_4$ and subsequent reduction.

Regarding the various meanings of $R_4$, present in the different reactives, these reactives are available in the market, or can be prepared according to well-known methods in literature, which the experts in the field can resort to, completing with their own knowledge of the argument.

Pharmaceutically acceptable salts are obtained with conventional methods found in the literature, and do not necessitate of further disclosure.

The compounds disclosed in the present invention have reversible inhibiting activity of carnitine palmitoyltransferase (CPT). This activity allows their use as active ingredients in the preparation of medicaments useful for the treatment and prevention of hyperglycaemia, diabetes and disorders related thereto, such as, for example diabetic retinopathy, diabetic neuropathy. The compounds of the present invention are also useful as active ingredient for the treatment and prevention of cardiovascular disorders, such as congestive heart failure. The compounds of formula (I) are also applicable for medicaments for the prevention and treatment of ketonic states, wherein it is intended the pathological conditions characterized by high levels of ketone bodies in blood.

Inhibiting activity mainly occurs on the isoform I of palmitoyl carnitine transferase (CPT-I).

A further object of the present invention relates to pharmaceutical compositions comprising at least a compound of formula (I), in an amount such as to produce a significant therapeutical effect. The compositions according to the present invention are conventional and are obtained with commonly used methods in the pharmaceutical industry. According to the desired administration route, the compositions shall be in solid or liquid form, suitable to the oral, parenteral, intravenous or transdermal route. The compositions according to the present invention comprise together with the active ingredients at least a pharmaceutically acceptable vehicle or excipient. Formulation co-adjuvants, for example solubilizing, dispersing, suspending, emulsionating agents can be particularly useful. Examples of suitable oral pharmaceutical compositions are capsules, tablets, granulates, powders, syrups, elixirs. Examples of suitable parenteral pharmaceutical compositions are solutions, emulsions, suspensions. Examples of suitable transdermal pharmaceutical compositions are patches, subcutaneous implants.

The compounds of formula (I) can also be used in combination with other well-known active ingredients.

The dose of the active ingredients will vary depending on the kind of active ingredient used, the administration route, the grade of pathology to be treated and the general conditions of the subject. The dosage and posology shall be determined by the clinic expert or the physician. Generally, a therapeutic effect can be obtained at dosages comprised between 1 and 100 mg/kg body weight.

The compounds according to the present invention are useful as medicaments with hypoglycaemic activity. A further object of the present invention is the preparation of a pharmaceutical composition comprising admixing at least a compound of formula (I) with suitable pharmaceutically acceptable excipients and/ or vehicles.

The following examples further illustrate the invention.

EXAMPLE 1

R,S-4-trimethylammonium-3-(nonylcarbamoyl)-aminobutyrate (ST 1251)

Nonyl Isocyanate

A solution of decanoyl chloride (20 g, 104.8 mmoles) in acetone (30 ml) was dropped into a solution of sodium azide (9.53 g, 146.6 mmoles) in water (30 ml), cooled in an ice bath. The temperature of the azide solution was kept between 10 and 15° C. after one hour, the solution was transferred in a separatory funnel and the lower phase (the aqueous one) was eliminated. The higher phase was transferred into a flask containing 100 ml of toluene, previously warmed at 65° C. After 1.5 hours, the solution was evaporated to dryness, giving 13.37 g crude product, which after vacuum distillation gave 8.3 g pure product in the form of colourless liquid.

Yield 47%. $^1$H-NMR (300 MHz; $CDCl_3$): δ: 3.3 (t, 2H), 1.6 (m, 2H), 1.45–1.2 (m, 12H), 0.9 (brt, 3H).

R,S-4-trimethylammonium-3-(nonylcarbamoyl)-aminobutyrate

Nonyl isocyanate (15.42 g, 91.12 mmoles) was added to a solution of aminocarnitine, inner salt (7.3 g, 45.56 mmoles) in anhydrous DMSO (350 ml) and the solution was left to stand for 60 hours at 40° C. The resulting mixture was transferred in a 3 l Erlenmeyer flask, containing ethyl ether (2.5 l) and the solvent was separated by decanting the formed precipitate, which was then transferred into a flask and precipitated again with ethyl ether. The so obtained crude product was washed several times with ethyl ether and purified on a silica gel chromatographic column, using a $CHCl_3$: MeOH 9:1 to $CHCl_3$: MeOH 3:7 gradient until elution of impurities with higher Rf, then eluting the product of interest with MeOH only. 9.7 g of pure product were obtained.

Yield 68%. M.p.: 145–147° C. $^1$H-NMR (300 MHz; $D_2O$): δ: 4.4 (m, 1H), 3.45 (dd, 1H), 3.30 (d, 1H), 3.05 (s, 9H), 2.9 (t, 2H), 2.3 (d, 2H), 1.3 (m, 2H), 1.15 (brs, 12H), 0.8 (brt, 3H). FAB Mass=330, [$(M+H)^+$]. Elemental analysis: responding to the expected formula $C_{17}H_{35}N_3O_3$. K.F.= 2.5% water. TLC silica gel $CHCl_3$: iPrOH:MeOH:$H_2O$:$CH_3COOH$ 42:7:28:10.5; Rf=0.55. HPLC: SGE-SCX column (5 μm, 250×4 mm), T=30° C., mobile phase 0.2 M $KH_2PO_4$:$CH_3CN$ 85:15, pH as such, flow 0.75 ml/min, detector: RI, UV 205 nm, RT=12.63 min.

EXAMPLE 2

R,S-4-quinuclidinium-3-(tetradecyloxycarbonyl)-oxybutyrate (ST 1265)

ter-Butyl R,S-4-guinuclidinium-3-hydroxybutyrate Iodide

Quinuclidine (2.40 g, 21.60 mmoles) was added to ter-Butyl R,S-4-iodo-3-hydroxybutyrate (6.18 g, 21.60 mmoles) in acetonitrile (60 ml) and the solution was warmed to 60° C. for 20 hours under stirring. After evaporation of the solvent, the residue was dissolved in acetonitrile and precipitated with ethyl ether several times to give 7.2 g of product, contaminated with about 13% by weight of quinuclidine iodide (as from NMR). After repeated crystallization from $CH_3CN$/$Et_2O$, 4.3 g of pure product were obtained.

Yield 50%. M.p.: 124–127° C. $^1$H-NMR (300 MHz; $D_2O$): δ: 4.50 (m, 1H), 3.40 (m, 2H), 2.42 (m, 2H), 2.08 (m, 1H), 1.88 (m, 6H), 1.34 (m, 9H). FAB Mass=270, [$M^+$]. Elemental analysis: responding to the expected formula $C_{15}H_{28}INO_3$. K.F.=0.5% water. The preparation of ter-butyl 4-iodo-3-hydroxybutyrate was carried out as described in J. Pharm. Science 64/7, 1262–1264, 1975.

Tetradecyl Chloroformate 29 ml of a 20% toluene solution of phosgene (55.98 mmoles) was added to tetradecyl alcohol (4 g, 18.66 mmoles) and the reaction mixture was left to stand for 20 hours under stirring at room temperature. After solvent evaporation, the residue was taken up with hexane and evaporated to dryness (several times) to give 5.1 g product as colourless liquid.

Yield 98%. $^1$H-NMR (300 MHz; $CDCl_3$): δ: 4.30 (t, 2H), 1.72 (m, 2H), 1.30 (m, 22H), 0.85 (brt, 3H).

ter-butyl R,S-4-guinuclidinium-3-(tetradecyloxycarbonyl)-oxy butyrate chloride

Dimethylaminopyridine (922 mg, 755 mmoles) and tetradecyl chloroformate (2.09 g, 7.55 mmoles) were added to ter-butyl R,S-4-quinuclidinium-3-hydroxybutyrate (2 g, 5.03 mmoles) in anhydrous $CH_2Cl_2$ (20 ml). The solution was left to stand at room temperature for 20 hours under stirring. After this time, the solution was diluted with $CHCl_3$, saturated with NaCl, and dried over anhydrous sodium sulfate. The dry residue obtained after evaporation was taken up with ethyl ether and the undissolved residue was filtered off. After solvent evaporation a crude product was obtained. Flash-chromatography ($CHCl_3$: MeOH 9:1) and elution with MeOH on Amberlyst A-21 resin (activated in HCl from), gave 1.6 g product as chloride.

Yield 58%. M.p.: 59–60° C. $^1$H-NMR (300 MHz; $CDCl_3$): δ: 5.50 (m, 1H), 4.55 (d, 2H), 3.80 (m, 7H), 2.90 (dd, 1H), 2.75 (dd, 1H), 2.22 (m, 1H), 2.05 (d, 6H), 1.65 (m, 2H), 1.41 (s, 9H), 1.25 (m, 22H), 0.85 (brt, 3H). FAB Mass=510, [$M^+$]. Elemental analysis: responding to the expected formula $C_{30}H_{56}ClNO_5$. K.F.=1.5% water.

R,S-4-guinuclidinium-3-(tetradecyloxycarbonyl)-oxybutyrate

Trifluoroacetic acid (6 ml) was added to ter-butyl R,S-4-quinuclidinium-3-(tetradecyloxycarbonyl)-oxybutyrate chloride (1.05 g, 1.92 mmoles) and the solution was left to stand for 1 hour at room temperature under stirring. After vacuum-evaporation of trifluoroacetic acid, the residue was taken up with cyclohexane and evaporated to dryness several times, then transferred on an Amberlyst IRA 402 resin ($Cl^-$ form) and eluted with water. The crude product, obtained by freeze-drying was purified through silica gel flash-chromatography ($CHCl_3$: MeOH 8:2) giving 480 mg product as inner salt.

Yield 55%. M.p: 132–134° C. $^1$H-NMR (300 MHz; $D_2O$): δ: 5.35 (m, 1H), 4.05 (m, 2H), 3.40 (m, 8H), 2.55 (dd, 1H), 2.35 (dd, 1H), 2.08 (m, 1H), 1.90 (m, 6H), 1.55 (m, 2H), 1.20 (m, 22H), 0.75 (brt, 3H). FAB Mass=454, [$(M+H)^+$. Elemental analysis: responding to the expected formula $C_{26}H_{47}NO_5$ K.F.=1.5% water. TLC silica gel $CHCl_3$:MeOH 7:3. Rf=0.34. HPLC: SGE-SCX column (5 μm, 250×4 mm), T=30° C., mobile phase 0.05 M $(NH_4)H_2PO_4$:$CH_3CN$ 60:40, pH 4.0, flow 0.75 ml/min, detector: RI, UV 205 nm, RT=6.72 min.

EXAMPLE 3

R,S-4-trimethylammonium-3-(nonylcarbamoyl)-oxybutyrate (ST 1298)

Benzyl ester of R,S-4-trimethylammonium-3-(nonylcarbamoyl)-oxybutyric acid perchlorate Nonyl isocyanate (7.39 g, 43.36 mmoles) was added to a solution of R,S-carnitine perchlorate, benzyl ester (7.69 g, 21.86 mmoles) in toluene (100 ml) and the solution was refluxed for 5 days under stirring. Nonyl isocyanate (1.84 g, 10.86 mmoles) was further added and the reaction mixture was left under reflux for other 5 days. The solvent was vacuum-evaporated and the residue was washed with ethyl ether and subsequently taken up with chloroform, washed with water and dried over anhydrous sodium sulfate. The oil resulting from the evaporation of the organic phase was purified through flash-chromatography column, using a gradient $CHCl_3$ to $CHCl_3$: MeOH 95:5. 4.4 g product were obtained in the form of a thick oil.

Yield 38.6%. $^1$H-NMR (200 MHz; $CDCl_3$): δ: 7.3 (s, 5H), 5.4 (m, 2H), 5.05 (m, 2H), 3.8 (dd, 1H), 3.55 (d, 1H), 3.15 (s, 9H), 3.05 (m, 2H), 2.75 (m, 2H), 1.4 (m, 2H), 1.2 (brs, 12H), 0.8 (brt, 3H). TLC silica gel $CHCl_3$: MeOH 9:1; Rf=0.29.

R,S-4-trimethylammonium-3-(nonylcarbamoyl)-oxybutyrate

10% Pd/C (0.44 g) was added to benzyl ester of R,S-4-trimethylammonium-3-(nonylcarbamoyl)-oxybutyric acid perchlorate (4.4 g, 8.44 mmoles) in MeOH (115 ml) and the mixture was hydrogenated at 47 psi for 4 hours. After filtration on celite, the solution was vacuum-concentrated and passed through an Amberlyst A-21 resin, eluting with MeOH. After solvent evaporation, 2.47 g product were obtained.

Yield 88.7%. M.p.: 151–153° C. $^1$H-NMR (300 MHz; $D_2O$): δ: 5.4 (m, 1H), 3.75 (dd, 1H), 3.5 (d, 1H), 3.15 (s, 9H), 3.05 (t, 2H), 2.55 (dd, 1H), 2.40 (dd, 1H), 1.45 (m, 2H), 1.20 (brs, 12H), 0.8 (brt, 3H). FAB Mass=331, [$(M+H)^+$]. Elemental analysis: responding to the expected formula $C_{17}H_{34}N_2O_4$. K.F.=1.5% water. TLC silica gel MeOH. Rf=0.22. HPLC: SPHERISORB-SCX column (5 μm, 250×4 mm), T=35° C., mobile phase 50 mM $KH_2PO_4$:$CH_3CN$ 40:60, pH 4.0 with $H_3PO_4$, flow 0.75 ml/min, detector: RI, UV 205 nm, RT=5.33 min.

EXAMPLE 4

R,S-4-trimethylammonium-3-(nonyloxycarbonyl)-oxybutyrate chloride (ST 1297)

Benzyl ester of R,S-4-trimethylammonium-3-(nonylcarbamoyl)-oxybutyric Acid Chloride Dimethylaminopyridine (3.8 g, 31.2 mmoles) and nonyl chloroformate (6.45 g, 31.2 mmoles) were added to R,S-carnitine perchlorate, benzyl ester (7.33 g, 20.8 mmoles) in anhydrous DMF (50 ml) at 0° C. The temperature was left to raise to room temperature and the reaction mixture was left to stand for 3 days under stirring. $CHCl_3$ was added and the solution was washed with 1N perchloric acid. The organic phase was dried over anhydrous sodium sulfate and evaporated to dryness, to give 6.02 g crude product, which was purified through flash-chromatography ($CHCl_3$: MeOH 85:15). 3.52 g a thick oil were obtained, which were subsequently dissolved in MeOH and passed through an Amberlyst A-21 resin (activated in HCl from), eluting with MeOH. After vacuum-evaporation of the solvent, 3.1 g oily product were obtained.

Yield 32.4%. $^1$H-NMR (200 MHz; $CDCl_3$): δ: 7.3 (s, 5H), 5.45 (m, 1H), 5.05 (s, 2H), 4.4 (d, 1H), 4.1 (t, 2H), 3.8 (dd, 1H), 3.4 (s, 9H), 2.9 (m, 2H), 1.55 (m, 2H), 1.2 (brs, 12H), 0.8 (brt, 3H).

Mutatis mutandis, the preparation of nonyl chloroformate was carried out as disclosed in Example 2 for tetradecyl chloroformate.

R,S-4-trimethylammonium-3-(nonyloxycarbonyl)-oxybutyric Acid Chloride

10% Pd/C (110 mg) was added to benzyl R,S-4-trimethylammonium-3-(nonyloxycarbonyl)-oxybutyric acid chloride (1.1 g, 2.4 mmoles) in MeOH (10 ml) and the mixture was hydrogenated at 47 psi for 2 hours. After filtration on celite, the solution was vacuum-dried giving 883 mg product (yield 100%), which was further purified by precipitation from $CH_3CN/Et_2O$. 600 g of product were obtained.

Yield: 68%. M.p.: 150° C. dec. $^1$H-NMR (300 MHz; $D_2O$): δ: 5.4 (m, 1H), 4.1 (m, 2H), 3.75 (dd, 1H), 3.55 (d, 1H), 3.1 (s, 9H), 2.7 (m, 2H), 1.5 (m, 2H), 1.20 (brs, 12H), 0.7 (brt, 3H). FAB Mass=332, [$M^+$]. Elemental analysis: responding to the expected formula $C_{17}H_{34}ClNO_5$. K.F.=1.7% water. TLC silica gel $CHCl_3$:MeOH 1:1, Rf=0.10. HPLC: SPHERISORB-Cl column (5 μm, 250×4.6 mm), T=30° C., mobile phase 50 mM $(NH_4)H_2PO_4$:$CH_3CN$ 60:40, pH 3.0 with $H_3PO_4$, flow 0.75 ml/min, detector: RI, UV 205 nm, RT=5.67 min.

EXAMPLE 5

R,S-4-trimethylphosphonium-3-(nonylcarbamoyl)-oxybutyrate (ST 1300)

Ethyl ester of R,S-4-trimethylphosphonium-3-hydroxybutyric Acid Iodide

A 1M solution of trimethylphosphine in THF (93 ml) was added to ethyl R,S-4-iodo-3-hydroxybutyrate (20 g, 77.5 mmoles) and the reaction mixture was left to stand at room temperature for 5 days under stirring. Ethyl ether was added, and the precipitate formed was separated by decantation. The precipitate was triturated with $Et_2O$ and dried under vacuum, giving 18.5 g product.

Yield 71.3%. M.p.: 105–107° C. $^1$H-NMR (200 MHz; $CDCl_3$): δ: 4.6 (m, 1H), 4.15 (q, 2H), 3.1 (m, 1H), 2.75 (m, 3H), 2.2 (d, 9H), 1.3 (t, 3H).

The ethyl ester of R,S-4-trimethylphosphonium-3-hydroxybutyric acid was prepared as described in Tetrahedron 1990, 4277–4282, starting from R,S-3-hydroxy-4-butyrolactone.

Ethyl ester of R,S-4-trimethylphosphonium-3-(nonylcarbamoyl)-oxybutyric Acid Iodide Nonyl isocyanate (4.04 g, 23.86 mmoles) was added to the ethyl ester of R,S-4-trimethylphosphonium-3-hydroxybutyric acid iodide (4 g, 11.97 mmoles) in anhydrous DMF (80 ml) and the solution was left to stand for 7 days at 110° C. under stirring. $CHCl_3$ was added (300 ml) and the solution was washed with water and dried over $Na_2SO_4$. The residue obtained after evaporation of the solvent was taken up with acetonitrile, the formed solid was filtered off and the filtrate was purified by silica gel flash-chromatography, using $CHCl_3$: MeOH 8:2. 2.07 g of product in the form of a thick oil were obtained.

Yield 34.3%. $^1$H-NMR (200 MHz; $CDCl_3$): δ: 5.4 (m, 2H), 4.15 (q, 2H), 3.15 (m, 4H), 2.8 (d, 2H), 2.2 (d, 9H), 1.5 (m, 2H), 1.2 (brs, 12H), 0.8 (brt, 3H).

R,S-4-trimethylphosphonium-3-(nonylcarbamoyl)-oxybutyrate Ethyl ester of R,S-4-trimethylphosphonium-3-(nonylcarbamoyl)-oxybutyric acid iodide (2.07 g, 4.11 mmoles) was dissolved into 1N HCl (200 ml) and the solution was warmed to 70° C. for 3 hours. The residue obtained after solvent vacuum-evaporation was taken up with MeOH and passed through Amberlyst A-21 resin, eluting with MeOH. A crude product was obtained, which was purified by flash-chromatography, eluting with MeOH and giving 700 mg product.

Yield: 49%. M.p.: 123–127° C. dec. $^1$H-NMR (300 MHz; $D_2O$): δ: 5.3 (m, 1H), 3.1 (m, 2H), 2.80–2.45 (m, 4H), 1.85 (d, 9H), 1.4 (m, 2H), 1.2 (brs, 12H), 0.8 (brt, 3H). FAB Mass=348, [$(M+H)^+$]. Elemental analysis: responding to the expected formula $C_{17}H_{34}$ $NO_4P$. K.F.=3.4% water. TLC silica gel MeOH; Rf=0.18.

HPLC: SPHERISORB-SCX column (5 μm, 250×4 mm), T=25° C., mobile phase 50 mM $KH_2PO_4$:$CH_3CN$ 40:60, pH 4.0 with $H_3PO_4$, flow 0.75 ml/min, detector: RI, UV 205 nm, RT=5.18 min.

The following Examples 6 and 7 are further illustrated by FIG. 1.

EXAMPLE 6

R,S-4-trimethylammonium-3-(octyloxycarbonyl)-aminobutyrate chloride (ST 1253) (2a, FIG. 1)

Step A 3 g (0.012 mmoles) aminocarnitine isobutyl ester were dissolved into 20 ml anhydrous $CH_2Cl_2$. 2.48 ml (0.1078 moles) triethylamine and 3.6 g (0.0178 moles) octyl chloroformate (previously prepared by reacting the alcohol with a toluene solution of phosgene) were added to the solution. The reaction mixture was left to stand for 4.5 hours at room temperature. Then the solvent was evaporated off and the resulting solid was dissolved into ethyl acetate and filtered. The solvent was vacuum-evaporated to dryness and the resulting solid was purified on silica gel, eluting with 100% $CHCl_3$, then with $CHCl_3$:MeOH 95:5 and 90:10. The product was obtained with a 50% yield.

TLC silica gel ($CHCl_3$ 42/MeOH 28/isopropyl alcohol 7/water 10.5/acetic acid 10.5)/acetone 7:3; Rf=0.8. HPLC: SPHERISORB-SCX column (5 μm, 250×4 mm), mobile phase 50 mM $(NH_4)H_2PO_4$:$CH_3CN$ 60:40, pH 4.0, detector: RI, UV 205 nm, RT=8.6 min. $^1$H-NMR (300 MHz; $CD_3OD$): δ: 4.56–4.46 (m, 1H), 4.12–4.02 (m, 2H), 3.94–3.88 (m, 2H), 3.66–3.5 (s, 9H), 3.4 (s, 9H), 2.74–2.66 (m, 2H), 2–1.86 (m, 1H), 1.68–1.56 (t, 2H), 1.4–1.2 (m, 12H), 0.97–0.7 (d, 6H), 0.6–0.3 (t, 3H). Elemental analysis: responding to the expected formula $C_{20}H_{41}$ $N_2O_4Cl$.

Step B

The ester obtained in step A was hydrolysed on Amberlyst IRA 402 resin ($OH^-$ activated form) eluting with water. Water was evaporated to dryness; the resulting solid was triturated with acetone and subsequently filtered. A white solid was obtained.

Yield 94%. M.p.=170° C. dec. $^1$H-NMR (300 MHz; $CD_3OD$): δ: 4.4 (m, 1H), 4.05 (t, 2H), 3.5 (d, 2H), 3.2 (s, 9H), 2.4 (d, 2H), 1.6 (m, 2H), 1.4–1.2 (m, 12H), 0.95–0.85 (t, 3H). FAB Mass=454, [$(M+H)^+$. Elemental analysis: responding to the expected formula $C_{16}H_{32}N_2O_4$ K.F.=1.74% water. TLC silica gel ($CHCl_3$ 42/MeOH 28/isopropyl alcohol 7/water 10.5/acetic acid 10.5) Rf=0.65. HPLC: SGE-SCX column (5 μm, 250×4 mm), mobile phase 0.05M $(NH_4)H_2PO_4$:$CH_3CN$ 60:40, detector: RI, UV 205 nm, RT=9.0 min.

EXAMPLE 7

R,S-4-trimethylammonium-3-(nonyloxycarbonyl)-aminobutyrate (ST 1285) (2b, FIG. 1)

Step A

The product was prepared as disclosed in Example 6, step A, using nonyl.chloroformate Yield: 50%. TLC silica gel ($CHCl_3$ 42/MeOH 28/isopropyl alcohol 7/water 10.5/acetic acid 10.5)/acetone 7:3 Rf=0.71. HPLC: SGE-SCX column (5 μm, 250×4 mm), mobile phase 50 mM $(NH_4)H_2PO_4$:$CH_3CN$ 60:40, pH 4.0, detector: RI, UV 205 nm, RT=10.417 min. $^1$H-NMR (300 MHz; $CD_3OD$): δ: 4.54–4.44 (m, 1H), 4.1–4.02 (m, 2H), 3.96–3.86 (m, 2H), 3.6–3.5 (m, 2H), 3.2 (s, 9H), 2.72–2.66 (m, 2H), 2–1.86 (m, 1H), 1.66–1.56 (m, 2H), 1.38–1.26 (m, 14H), 0.96–0.94 (d, 6H), 0.92–0.86 (t, 3H).

Step B

The product was prepared as disclosed in Example 6, step B.

Yield 80%. M.p.=160° C. dec. $^1$H-NMR (300 MHz; $CD_3OD$): δ: 4.5–4.35 (m, 1H), 4.1–4.0 (t, 2H), 3.55–3.45 (d, 2H), 3.2 (s, 9H), 2.45–2.35 (d, 2H), 1.7–1.5 (m, 2H), 1.4–1.2 (m, 14H), 0.9–0.8 (t, 3H). Elemental analysis: responding to the expected formula $C_{17}H_{34}N_2O_4$ K.F.=1.3 % water. TLC silica gel ($CHCl_3$ 42/MeOH 28/isopropyl alcohol 7/water 10.5/acetic acid 10.5); Rf=0.62. HPLC: SGE-SCX column (5 μm, 250×4 mm), mobile phase 0.05M $(NH_4)H_2PO_4$:$CH_3CN$ 60:40, detector: RI, UV 205 nm, RT=7.56 mm.

Figure 2:
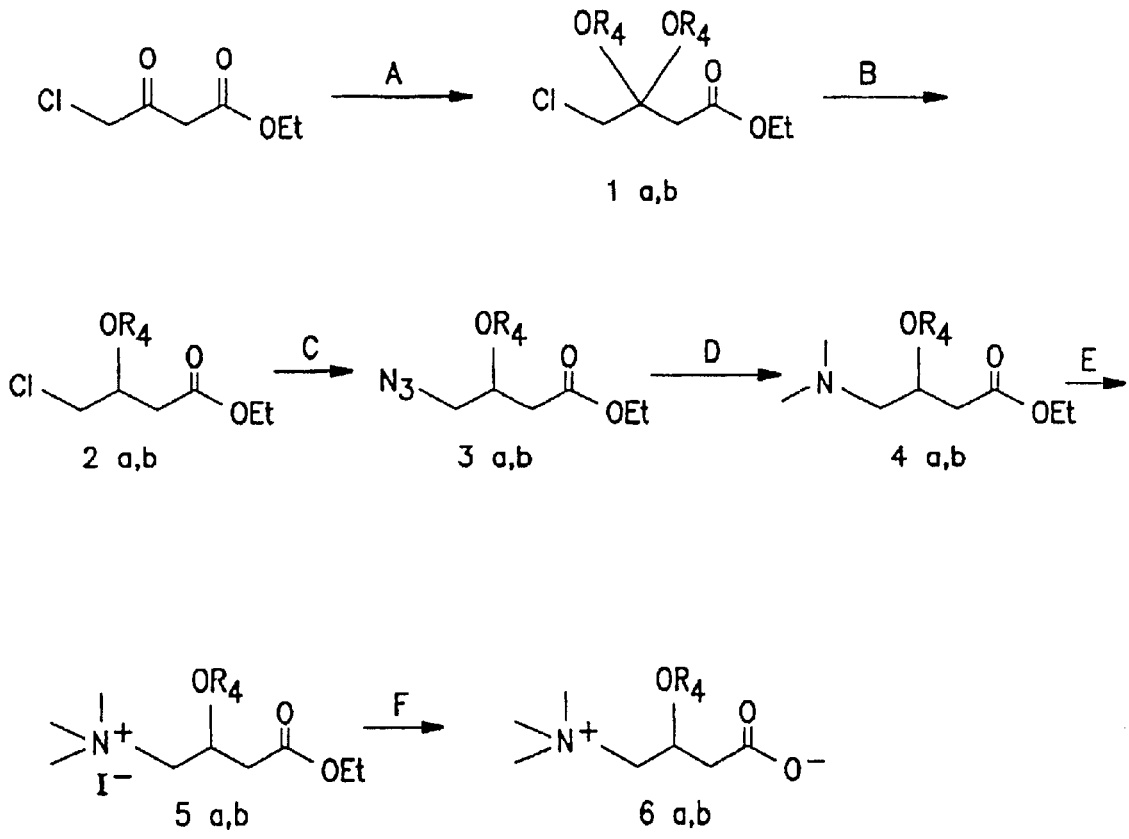
*FIG. 2 is a flow chart illustrating examples 8 and 9;*

The following Examples 8–9 are further illustrated by FIG. 2.

EXAMPLE 8

R,S-4-trimethylammonium-3-octyloxybutyrate (ST 1207) (6a, FIG. 2)

Step A 39 g (0.3 moles) octyl alcohol were dissolved in 25 ml toluene and 14.5 ml (0.107 moles) ethyl chloroacetate and 8 ml Thionyl chloride were added thereto at −15° C. At the end of the addition, the reaction mixture was left to stand for 4 hours at room temperature. Ethyl acetate was then added and the solution was washed three times with 1N NaOH and subsequently with water. The organic phase was treated with anhydrous sodium sulfate, filtered and vacuum-evaporated to dryness. The product was purified on silica gel chromatographic column, eluting with gradient from hexane alone to hexane/ethyl ether 95:5. The product was obtained with 80% yield.

TLC silica gel hexane/ethyl ether 85:15; Rf=0.75. $^1$H-NMR (300 MHz; $CDCl_3$): δ: 4.2–4.09 (q, 2H), 3.80 (s, 2H), 3.4–3.5 (dd, 2H), 2.85 (s, 2H), 1.60–1.58 (m, 2H), 1.4–1.2 (m, 10H), 0.90–0.80 (t, 3H). Elemental analysis: responding to the expected formula $C_{22}H_{33}$ $ClO_4$.

Step B 9 ml $BF_3$:$Et_2O$ were dropped to a mixture of 26.8 g (0.066 moles) of the product obtained in the preceding step A and 13.5 ml triethylsilane at 0° C. At the end of the addition, the reaction mixture was refluxed for 4 hours. After cooling, ether was added and the solution was washed twice with NaOH 1N, then water; the organic phase was dried over anhydrous sodium sulfate, filtered and vacuum-evaporated to dryness. An oil was obtained, which was purified on silica gel chromatographic column, eluting with gradient from hexane alone to hexane/ethyl ether 95:5. The product was obtained with a 70% yield.

TLC silica gel hexane/ethyl ether 90:10; Rf=0.47. $^1$H-NMR (300 MHz; $CDCl_3$): δ: 4.2–4.09 (dd, 2H), 4.0–3.85 (m, 1H), 3.62–3.40 (m, 4H), 2.70–2.50 (dd, 2H), 1.55–1.50 (m, 2H), 1.4–1.2 (m, 10H), 0.90–0.80 (t, 3H). Elemental analysis: responding to the expected formula $C_{14}H_{27}ClO_3$ Step C 5.2 g (0.08 moles) $NaN_3$ and a catalytic amount of tetrabutyl ammonium bromide were added to a solution of 11.4 g (0.041 moles) product obtained in the preceding step B. The reaction mixture was left for three nights at 60° C. The solution was vacuum-evaporated to dryness. A thick dark solution was obtained, which was purified on silica gel chromatographic column, eluting with gradient from hexane alone to hexane/ethyl ether 95:5. The product was obtained with a 83% yield.

TLC silica gel hexane/ethyl ether 95:5; Rf=0.23. $^1$H-NMR (300 MHz; $CDCl_3$): δ: 4.2–4.09 (dd, 2H), 4.0–3.80 (m, 1H), 3.60–3.40 (dd, 2H), 3.40–3.20 (dd, 2H), 2.70–2.40 (dd, 2H), 1.60–1.40 (m, 2H), 1.4–1.1 (m, 10H), 0.90–0.80 (t, 3H). Elemental analysis: responding to the expected formula $C_{14}H_{27}N_3O_3$.

Step D

The product obtained in the preceding step C (15.39 g, 0.054 moles) was dissolved in 31 ml of acetic acid and the resulting solution was subjected to catalytic hydrogenation with 10% Pd/C at 60 psi for 7 hours. The reaction progress was checked by TLC, until disappearance of the starting product (hexane/ethyl ether 95:5). Thereafter, formaldehyde was added (4.6 ml, 0.167 moles) followed by 10% Pd/C and the mixture was hydrogenated at 30 psi for 2 days. The catalyst was filtered off and the mixture was vacuum-dried. A pale yellow liquid was obtained, which was taken up with methylene chloride, washed with 1N NaOH, then water, then NaCl saturated solution; the organic phase was dried over anhydrous sodium sulfate, filtered and vacuum-evaporated to dryness. A thick oil was obtained. The product was obtained with a 98% yield.

TLC silica gel AcOEt/MeOH/$NH_3$ 90:10:3; Rf=0.42. $^1$H-NMR (300 MHz; $CDCl_3$): δ: 4.2–4.09 (dd, 2H), 3.85–3.80 (m, 1H), 3.60–3.40 (dd, 2H), 2.65–2.40 (dd, 2H), 2.40–2.20 (dd, 2H), 2.20 (s, 6H), 1.60–1.40 (m, 2H), 1.4–1.1 (m, 10H), 0.90–0.80 (t, 3H). Elemental analysis: responding to the expected formula $C_{16}H_{36}NO_3$.

Step E

The product obtained in the preceding step D (15.21 g, 0.053 moles) was dissolved in 98 ml THF and 8 ml methyl iodide were added thereto. The reaction progress was left overnight at room temperature. The mixture was vacuum-evaporated to dryness. A thick oil was obtained. The product was obtained with a 98% yield.

TLC silica gel AcOEt/MeOH/$NH_3$ 90:10:3; Rf=0.10. $^1$H-NMR (300 MHz; $CDCl_3$): δ: 4.45–4.3 (m, 1H), 4.2–4.09 (dd, 2H), 3.75–3.30 (m, 2H), 3.5 (s, 9H), 2.75–2.60 (dd, 2H), 1.60–1.45 (m, 2H), 1.30–1.15 (m, 10H), 0.90–0.80 (t, 3H). Elemental analysis: responding to the expected formula $C_{16}H_{39}INO_3$.

Step F

The product obtained in the preceding step E, was hydrolysed on Amberlyst IRA 402 resin ($OH^-$ activated form) eluting with water. Water was evaporated to dryness; the resulting solid was treated with isopropyl alcohol three times. A white solid was obtained.

Yield=93% M.p.=106° C. dec. $^1$H-NMR (300 MHz; MeOD): δ: 4.30–4.15 (m, 1H), 3.70–3.60 (dd, 1H), 3.50–3.40 (m, 2H), 3.20 (s, 9H), 2.75–2.65 (dd, 1H), 2.20–2.10 (dd, 1H), 1.60–1.50 (m, 2H), 1.40–1.20 (m, 10H), 0.9–0.8 (t, 3H). Elemental analysis: responding to the expected formula $C_{15}H_{31}NO_3$. K.F.=5.7 % water. TLC silica gel ($CHCl_3$ 42/MeOH 28/isopropyl alcohol 7/water 10.5/acetic acid 10.5); Rf=0.7. HPLC: SGE-SAX column (5 μm, 250×4 mm), mobile phase 0.025M $(NH_4)H_2PO_4$:$CH_3CN$ 30:70, detector: RI, UV 205 nm, flow=0.75 ml/min, RT=5.85 min. MS-FAB+glycerol matrix=274.

EXAMPLE 9

R,S-4-trimethylammonium-3-tetradecyloxybutyrate (ST 1228) (6b, FIG. 2)

Step A

The product was prepared as in example 8, step A using tetradecyl alcohol. The product was obtained with 73% yield.

TLC silica gel hexane/ethyl ether 95:5; Rf=0.63. $^1$H-NMR (300 MHz; $CDCl_3$): δ: 4.2–4.09 (q, 2H), 3.80 (s, 2H), 3.4–3.5 (dd, 2H), 2.85 (s, 2H), 1.60–1.58 (m, 2H), 1.4–1.2 (m, 22H), 0.90–0.80 (t, 3H). Elemental analysis: responding to the expected formula $C_{34}H_{67}ClO_4$.

Step B

The product was prepared as in example 8, step B. The product 2b, shown in FIG. 2, was obtained with a 72% yield.

TLC silica gel hexane/ethyl ether 95:5; Rf=0.4. $^1$H-NMR (300 MHz; $CDCl_3$): δ: 4.2–4.09 (dd, 2H), 4.0–3.85 (m, 1H), 3.62–3.40 (m, 4H), 2.70–2.50 (dd, 2H), 1.55–1.50 (m, 2H), 1.4–1.2 (m, 22H), 0.90–0.80 (t, 3H). Elemental analysis: responding to the expected formula $C_{20}H_{39}O_3$.

Step C

The product was prepared as in example 8, step C. The product was obtained with 79% yield.

TLC silica gel hexane/ethyl ether 90:10; Rf=0.36. $^1$H-NMR (300 MHz; $CDCl_3$): δ: 4.2–4.09 (dd, 2H), 4.0–3.30 (m, 1H), 3.60–3.40 (dd, 2H), 3.40–3.20 (dd, 2H), 2.70–2.40 (dd, 2H), 1.60–1.40 (m, 2H), 1.4–1.1 (m, 22H), 0.90–0.80 (t, 3H). Elemental analysis: responding to the expected formula $C_{20}H_{39}N_3O_3$.

Step D

The product was prepared as in example 8, step D. The product was obtained with a 98% yield.

TLC silica gel AcOEt/MeOH/$NH_3$ 90:10:3; Rf=0.72. $^1$H-NMR (300 MHz; $CDCl_3$): δ: 4.2–4.09 (dd, 2H), 3.85–3.80 (m, 1H), 3.60–3.40 (dd, 2H), 2.65–2.42 (dd, 2H), 2.38–2.20 (dd, 2H), 2.18 (s, 6H), 1.60–1.40 (m, 2H), 1.4–1.1 (m, 22H), 0.90–0.80 (t, 3H). Elemental analysis: responding to the expected formula $C_{22}H_{45}NO_3$.

Step E

The product was prepared as in example 8, step E. The product was obtained with a 99% yield.

TLC silica gel AcOEt/MeOH/$NH_3$ 90:10:3; Rf=0.15. $^1$H-NMR (300 MHz; $CDCl_3$): δ: 4.45–4.3 (m, 1H), 4.2–4.09 (dd, 2H), 3.75–3.30 (m, 2H), 3.5 (s, 9H), 2.75–2.60 (dd, 2H), 1.60–1.45 (m, 2H), 1.30–1.15 (m, 22H), 0.90–0.80 (t, 3H). Elemental analysis: responding to the expected formula $C_{23}H_{48}INO_3$.

Step F

The product was prepared as in example 8, step F. The product was obtained with a 99% yield.

M.p.=106° C. dec. $^1$H-NMR (300 MHz; DMSO-D6): δ: 4.10–4.0 (m, 1H), 3.60–3.20 (m, 4H), 3.05 (s, 9H), 2.40–2.30 (dd, 1H), 1.80–1.70 (dd, 1H), 1.50–1.40 (m, 2H), 1.30–1.15 (m, 22H), 0.9–0.8 (t, 3H). Elemental analysis: responding to the expected formula $C_{21}H_{43}NO_3$. K.F.=6.4% water. TLC silica gel ($CHCl_3$ 42/MeOH 28/isopropyl alcohol 7/water 10.5/acetic acid 10.5); Rf=0.6. HPLC: SGE-SCX column (5 μm, 250×4 mm), mobile phase 0.05M $(NH_4)H_2PO_4$:$CH_3CN$ 40:60, detector: RI, UV 205 nm, flow=0.75 ml/min, RT=4.38 min. MS-FAB+glycerol matrix=358.3

Figure 3A:
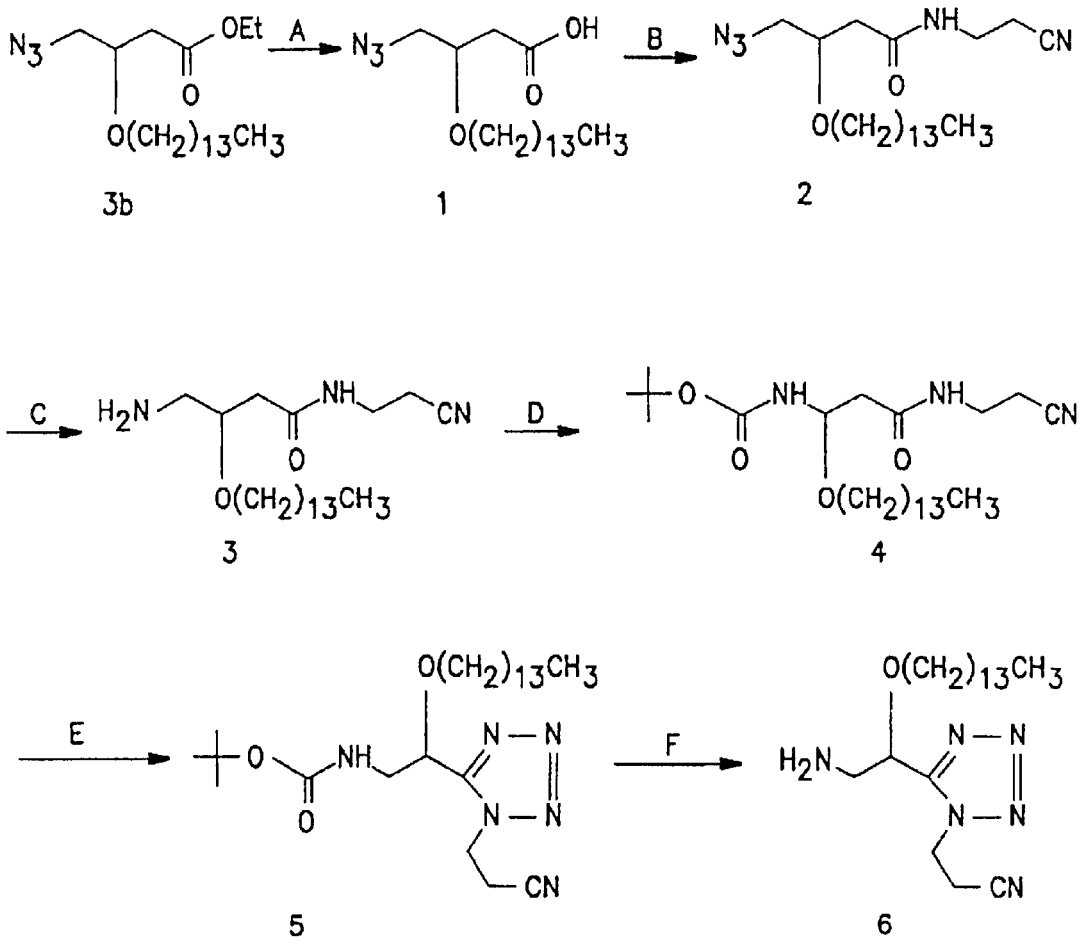
*FIG. 3A is a flow chart illustrating examples 10 and 11;*
Figure 3B:
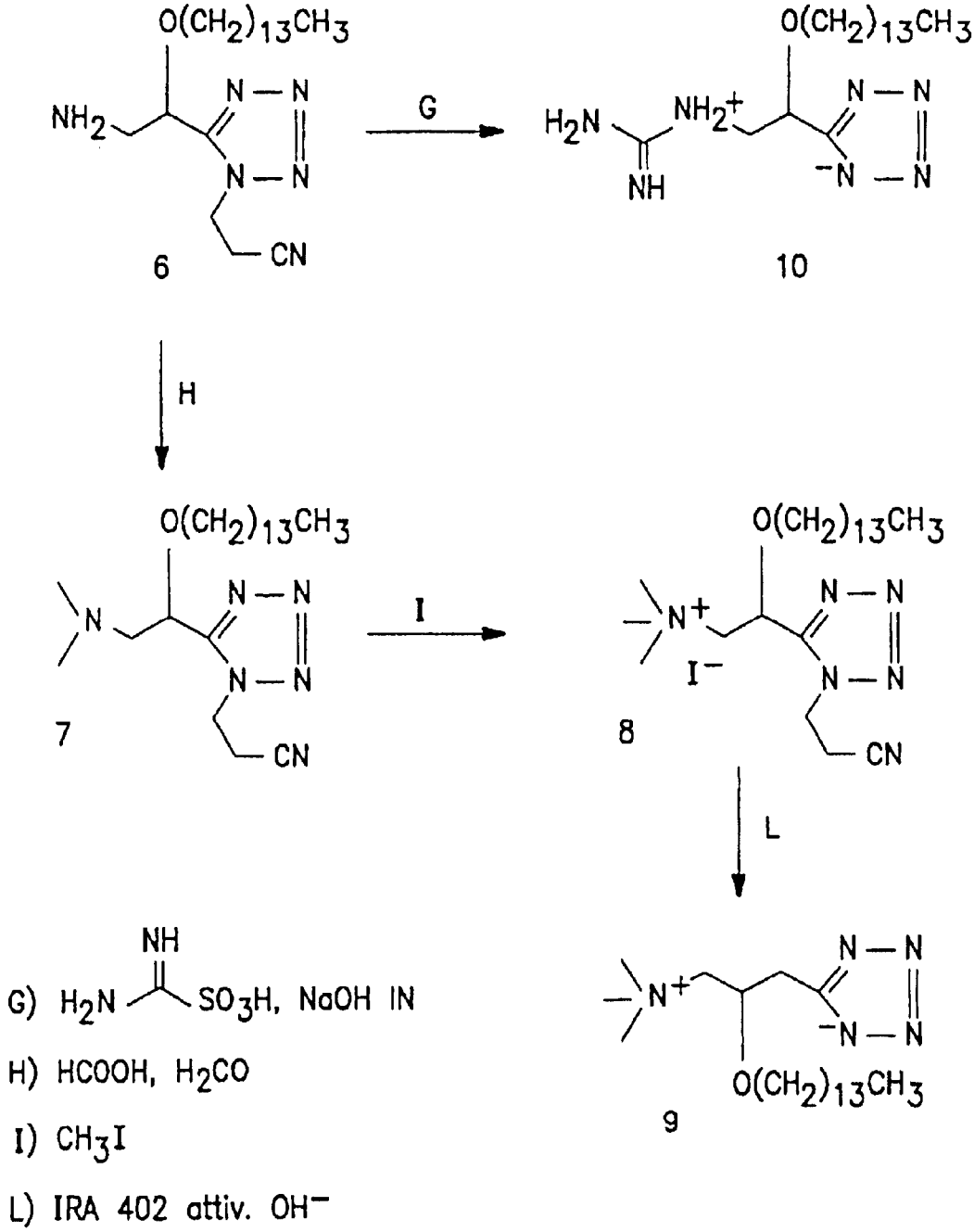
*FIG. 3B is a flow chart illustrating examples 10 and 11; and*

The following Examples 10–11 are further illustrated by FIGS. 3a–b.

EXAMPLE 10

R,S-1-guanidinium-2-tetradecyloxy-3-(tetrazolate-5-yl)propane (ST 1263) (10, FIG. 3b)

Step A 6.65 g (0.0179 moles) of the intermediate prepared in Example 9, step C were dissolved in 10 ml of methanol and 10 ml of 4N NaOH were added to the solution. The reaction was left to stand for 16 hours at room temperature. 20 ml 6N HCl were added to the solution, which was extracted with ethyl acetate. The organic phase was dried over anhydrous sodium sulfate, filtered and vacuum concentrated. The product was obtained as a white solid with a 95.6% yield.

TLC silica gel hexane/ethyl ether 1:1; Rf=0.5. M.p.=42–45° C. $^1$H-NMR (300 MHz; $CD_3OD$): δ: 3.9–3.8 (m, 1H), 3.56–3.48 (m, 2H), 3.42–3.26 (dd, 2H), 2.68–2.5 (m, 2H), 1.6–1.5 (m, 2H), 1.4–1.2 (s, 22H), 0.90–0.80 (t, 3H). Elemental analysis: responding to the expected formula $C_{18}H_{35}N_3O_3$.

Step B

At 0° C., 4.96 ml TEA were dropped into a solution containing 2.79 g (8.19 mmoles) of the compound obtained in step A, aminopropionitrile (0.58 g, 8.2 mmoles) and DEPC (diethylphosphocyanydate) (1.71 ml) in 4.2 ml of anhydrous DMF. The reaction was left to stand for 1 hour at room temperature. The solvent was evaporated and the residue was dissolved in ethyl acetate, washed twice with water, then with a NaCl saturated solution. The organic phase was dried over anhydrous sodium sulfate, filtered and vacuum concentrated. The product was obtained and purified through a silica gel column with hexane: ethyl ether (7:3/1:1/3:7).

Yield: 71%. TLC silica gel ethyl ether 100%; Rf=0.42. $^1$H-NMR (300 MHz; $CDCl_3$): δ: 6.6–6.4 (m, 1H), 3.9–3.8 (m, 1H), 3.60–3.4 (m, 5 H), 3.3–3.2 (dt, 1H), 2.7–2.6 (t, 2H), 2.6–2.4 (dd, 2H), 1.6–1.5 (m, 2H), 1.4–1.2 (m, 22H), 0.90–0.80 (t, 3H). Elemental analysis: responding to the expected formula $C_{21}H_{39}N_5O_2$ Step C 2.99 g (0.0114 moles) triphenylphosphine and 0.2 ml water were added to a solution containing 2.99 g (7.62 mmoles) of the compound obtained in step B. The reaction was left to stand overnight at room temperature. The solvent was evaporated off and the product was obtained and purified through a silica gel column with ethyl acetate 100%, then ethyl acetate:methanol:ammonia 7:3:0.3.

Yield: 65%. TLC silica gel ethyl acetate:methanol:ammonia 7:3:0.3; Rf=0.26. $^1$H-NMR (300 MHz; $CD_3OD$): δ: 3.78–3.7 (m, 1H), 3.58–3.48 (m, 4H), 2.8–2.7 (dd, 2H), 2.7–2.6 (m, 2H),. 2.5–2.3 (dd, 2H), 1.6–1.5 (m, 2H), 1.4–1.3 (m, 22H), 0.90–0.80 (t, 3H). Elemental analysis: responding to the expected formula $C_{21}H_{41}N_3O_2$.

Step D 1.69 g (4.6 mmoles) of the compound obtained in step C were treated with 1.2 g (5.2 mmoles) $(BOC)_2O$ and 9.2 ml 1N NaOH for 30 minutes at room temperature. The reaction mixture was poured into ethyl acetate and washed four times with 1N HCl, then water and a saturated NaCl solution. The organic phase was dried over anhydrous sodium sulfate, filtered and vacuum concentrated to dryness. The product was obtained as a white solid.

Yield: 100%. TLC silica gel ethyl ether 100%; Rf=0.26. M.p.=83–84° C. $^1$H-NMR (300 MHz; $CDCl_3$): δ: 7.2–7.0 (m, 1H), 4.9–4.8 (m, 1H), 3.8–3.6 (m, 1H), 3.5–3.4 (dt, 4H), 3.2–3.0 (m, 2H), 2.6 (t, 2H), 2.4 (d, 2H), 1.5 (m, 2H), 1.4 (s, 9H), 1.4–1.2 (m, 22H), 0.90–0.80 (t, 3H). Elemental analysis: responding to the expected formula $C_{26}H_{49}N_3O_4$.

Step E

The product obtained in step D (1.19 g, 2.56 mmoles) was dissolved into 12 ml of anhydrous THF, under -argon atmosphere, then 3.062 g of triphenylphosphine, 1.54 ml of triethylsilylazido and 4.9 ml of DEAD (diethylazodicarboxylate) were dropped at 0° C. within three days, until disappearance of the starting product. The mixture was then treated with an aqueous solution of cerium ammonium nitrate and diluted with $CH_2Cl_2$. The reaction was left to stand for 2 hours, the organic phase was washed with a saturated NaCl solution, dried over anhydrous sodium sulfate and vacuum-dried. The residue was purified through a silica gel column with hexane/ethyl acetate (9:1/8:2/7:3). The product was obtained with a 66% yield.

TLC silica gel hexane/AcOEt 1:1; Rf=0.34. $^1$H-NMR (300 MHz; $CDCl_3$): δ: 4.95–4.8 (m, 1H), 4.7–4.5 (m, 2H), 3.9–3.8 (m, 1H), 3.50–3.40 (m, 1H), 3.40–3.31 (m, 1H), 3.3–3.2 (m, 1H), 3.22–3.0 (dd, 2H),. 3.10–3.0 (m, 3H), 1.45–1.35 (m, 1H), 1.2 (m, 22H), 0.90–0.80 (t, 3H). Elemental analysis: responding to the expected formula $C_{15}H_{48}N_6O_3$ Step F The product obtained in step E (0.969 g, 1.97 mmoles) was dissolved into 13.09 ml anhydrous THF, then 13.1 ml of 3N HCl were added. The reaction mixture was left to stand for 2 hours, at 50° C. under stirring. The reaction mixture -was vacuum-dried, the residue was taken up with $CH_2Cl_2$ and treated with a 1N NaOH solution. The organic phase was separated, dried over anhydrous sodium sulfate and vacuum-dried. The product was obtained with a 92% yield.

TLC silica gel AcOEt/MeOH/$NH_3$ 9:1:0.3 Rf=0.31. $^1$H-NMR (300 MHz; $CDCl_3$): δ: 4.78–4.58 (m, 2H), 3.8–3.7 (m, 1H), 3.5–3.4 (m, 1H), 3.30–3.24 (m, 1H), 3.24–3.18 (m, 4H), 3.05–3.0 (dd, 2H), 3.0–2.6 (dd, 2H), 1.4 (m, 2H), 1.2 (m, 22H), 0.90–0.80 (t, 3H). Elemental analysis: responding to the expected formula $C_{21}H_{40}N_6O$ Step G The product obtained in step F (2.78 g, 7.1 mmoles) was dissolved into 20 ml anhydrous MeOH, then 2.34 g iminomethanesulfonic acid (prepared with well-known methods) were added within 3 days. The obtained suspension was vacuum-concentrated, then treated with 1N NaOH and left under stirring for 30 minutes. The solid was filtered, washed with water, then acetone. The title product was obtained with a 45% yield.

TLC silica gel AcOEt/MeOH/$NH_3$ 7:3:0.3; Rf=0.22. M.p.=240° C. dec.

$^1$H-NMR (300 MHz; $CD_3OD$): δ: 3.90–3.75 (m, 1H), 3.6–3.4 (m, 2H), 3.40–3.20 (m, 2H), 3.20–3.10 (dd, 1H), 2.95–2.85 (dd, 1H), 1.4 (m, 2H), 1.2 (s, 22H), 0.90–0.80 (t, 3H).

Elemental analysis: responding to the expected formula $C_{19}H_{39}N_7O$.

HPLC: Spherisorb-Cl (5 μm, 250×4.6 mm), mobile phase 0.05 M $KH_2PO_4$:$CH_3CN$ 35:65, pH=3, flow 0.75 ml/min, detector: UV 205 nm, RT=5.51 min.

MS-FAB+glycerol matrix=382.

EXAMPLE 11

R,S-1-trimethylammonium-2-tetradecyloxy-3-(tetrazolato-5-yl)propane (ST 1287) (9, FIG. 3b)

Steps A–F

The compounds were prepared as in steps A–F of Example 10.

Step H 2.79 g (7.14 mmoles) of the compound prepared in Example 10, step F were suspended in 18 ml water and 1.47 ml HCOOH and 1.57 ml $H_2CO$ were added thereto. The reaction mixture was refluxed overnight, then was allowed to cool down and methylene chloride was added; pH was adjusted to 9 with 0.5 N NaOH. The mixture was extracted three times with methylene chloride. The organic phase was washed with 0.5 N NaOH, water and dried over anhydrous sodium sulfate, filtered and vacuum concentrated. The product was obtained as a solid with a 100% yield.

TLC silica gel AcOEt/MeOH/$NH_3$ 9:1:0.3; Rf=0.58. $^1$H-NMR (300 MHz; $CDCl_3$): δ: 4.7–4.5 (m, 1H), 3.8–3.7 (m, 1H), 3.5–3.4 (m, 1H), 3.30–3.20 (m, 2H), 3.10 (m, 3H), 2.45–2.35 (m, 2H), 2.30 (s, 6H), 1.4–1.3 (m, 2H), 1.2–1.0 (m, 22H), 0.90–0.80 (t, 3H). Elemental analysis: responding to the expected formula $C_{23}H_{44}N_6O$.

Step I 2.99 g (7.14 mmoles) of the compound obtained in step H were dissolved in THF and 2.5 ml of $CH_3I$ were added thereto. The reaction was left to stand for 3 hours at room temperature. The solvent was evaporated off and the solid residue was washed with hot ether, left overnight under stirring, then filtered. The product was obtained.

Yield: 100%. TLC silica gel $CHCl_3$:iPrOH:MeOH:$H_2O$:$CH_3COOH$ 42:7:28:10.5:10.5; Rf=0.73. $^1$H-NMR (300 MHz; $CDCl_3$): δ: 4.90–4.80 (m, 2H), 4.70–4.55 (m, 1H), 4.40–4.25 (m, 1H), 3.80–3.60 (m, 2H), 3.60–3.40 (m, 3H), 3.30 (s, 9H), 3.30–3.10 (m, 2H), 1.60–1.40 (m, 2H), 1.3–1.1 (m, 22H), 0.9–0.8 (t, 3H). Elemental analysis: responding to the expected formula $C_{24}H_{47}IN_6O$. MS-FAB+glycerol matrix=436.

Step L

The product obtained in step I (2.99 g, 5.33 mmoles) was dissolved in MeOH, then passed through IRA 402 resin in $OH^-$ form, conditioned in MEOH. The title product was obtained as a solid, which was subsequently triturated with AcOEt.

Figure 4:
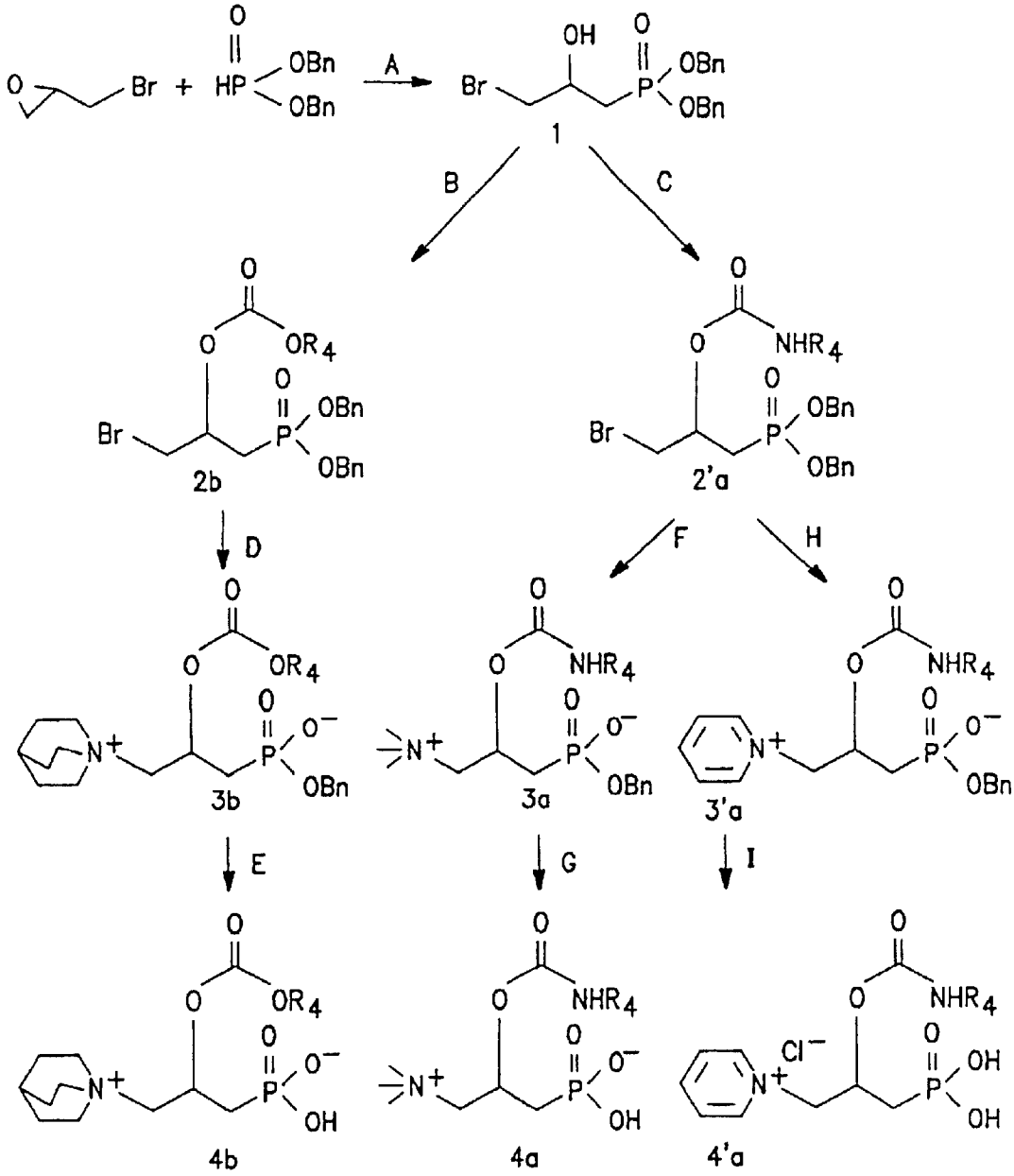
*FIG. 4 is a flow chart illustrating examples 12-14.*

Yield=88%. TLC silica gel $CHCl_3$:iPrOH:MeOH:$H_2O$:$CH_3COOH$ (42:7:28:10.5:10.5)/acetone 8:2; Rf=0.73. TLC silica gel $CHCl_3$:iPrOH:MeOH:$H_2O$:$CH_3COOH$ 42:7:28:10.5:10.5; Rf=0.73. M.p.=180° C. dec. $^1$H-NMR (300 MHz; $CDCl_3$): δ: 4.30–4.20 (m, 1H), 3.90–3.70 (m, 2H), 3.60–3.55 (m, 1H), 3.50–3.30 (m, 4H), 3.25 (m, 1H), 3.0–2.9 (m, 1H), 1.60–1.40 (m, 2H), 1.3–1.1 (m, 22H), 0.9–0.8 (t, 3H). Elemental analysis: responding to the expected formula $C_{21}H_{43}N_5O$. MS-FAB+glycerol matrix=382. K.F.=1% water HPLC: Spherisorb-Cl (5 μm, 250×4.6 mm), mobile phase 0.05 M $KH_2PO_4$:$CH_3CN$ 35:65, pH=3, flow 0.75 ml/min, detector: UV 205 nm, RT=5.18 min. The following Examples 12–14 are further illustrated by FIG. 4.

EXAMPLE 12

R,S-3-quinuclidinium-2-(tetradecyloxycarbonyl)-oxy-1-propanephosphonate monobasic (ST 1260)

Step A

In anhydrous environment, −70° C., a hexane solution of 1.6 M BuLi (14 ml, 0.022 moles) was dropped into a solution of dibenzyl phosphite (5.8 g, 0.022 mmoles) in THF. After 15 minutes, 1.8 ml (0.022 moles) of epibromhydrine, dissolved in 5 ml THF, were added. After the addition, etherated $BF_3$ (3.6 ml, 0.022 moles) was dropped very slowly. The reaction was left for further 3 hours at −70° C. A saturated ammonium chloride solution was added; then the temperature was left to raise to room temperature. This solution was extracted several times with AcOEt and the gathered organic phases were treated with saturated $NaHCO_3$, and dried over anhydrous sodium sulfate, filtered and vacuum concentrated. An oil was obtained, which after purification on silica gel chromatography (AcOEt/Hexane 1:1); gave 1.1 g of unreacted dibenzylphosphite and 5.3 g of product of interest.

Yield=60%. TLC silica gel AcOEt/Hexane 7:3; Rf=0.54. $^1$H-NMR (300 MHz; $CD_3OD$): δ: 7.4–7.2 (m, 10H), 5.1–4.9 (m, 4H), 4.2–4.0 (m, 1H), 3.5–3.3 (dd, 2H), 2.2–2.0 (m, 2H). Elemental analysis: responding to the expected formula $C_{17}H_{20}BrO_4P$. MS-FAB+glycerol matrix-399, 400, 401, 402.

Step B 2 g (5 mmoles) of the compound obtained in step A were dissolved at 10% concentration and the solution cooled down to 0° C. 1.4 ml TEA (10 mmoles) and 0.62 g (5 mmoles) DMAP (dimethylaminopyridine) were dropped thereto. Immediately after, 5.2 mmoles tetradecyl chloroformate were added and the temperature was left to raise to room temperature. The reaction progress was checked on TLC and worked up at the disappearance of the starting compound. Further chloroform was added and the reaction mixture was washed with 1N HCl and water. After drying over anhydrous sodium sulfate, the solvent was evaporated off and an oil was obtained, which was purified through flash-chromatography using hexane/AcOEt 7:3 as eluant. The product was obtained.

Yield: 75%. TLC silica gel hexane/AcOEt 7:3; Rf=0.31. $^1$H-NMR (300 MHz; $CDCl_3$): δ: 7.4–7.2 (m, 10H), 5.1–4.9 (m, 5H), 4.1–3.9 (m, 2H), 3.6–3.4 (dd, 2H), 2.4–2.2 (m, 2H), 1.6–1.4 (m, 2H), 1.3–1.1 (m, 22H), 0.9–0.7 (t, 3H). Elemental analysis: responding to the expected formula $C_{32}H_{48}BrO_6P$.

Step D

The product obtained in step B (6.39 g, 10 mmoles) was dissolved in 12 ml DMF, then quinuclidine was added (2.2 g, 20 mmoles) together with TBAI (tetrabutyl ammonium iodide) in catalytic amounts (1% by weight with respect to the substrate). The reaction was carried out at a temperature of 50° C., until the starting product disappeared. At the end of reaction, the mixture was concentrated under high vacuum, obtaining a semisolid containing the product. The latter was purified through silica gel flash-chromatography, using $CHCl_3$/MeOH 8.3. The product was obtained.

Yield=15%. TLC silica gel $CHCl_3$:iPrOH:MeOH:$H_2O$:$CH_3COOH$ (42:7:28:10.5:10.5)/acetone 8:2; Rf=0.8. $^1$H-NMR (300 MHz; MeOD): δ: 7.4–7.1 (m, 50H), 5.3–5.1 (m, 1H), 4.9–4.8 (d, 2H), 4.1–4.0 (m, 2H), 3.8–3.4 (m, 2H), 3.4–3.2 (m, 6H), 2.2–1.7 (m, 9H), 1.6–1.4 (m, 2H), 1.3–1.1 (m, 22H), 0.9–0.7 (t, 3H). Elemental analysis: responding to the expected formula $C_{32}H_{54}NO_6P$. MS-FAB+glycerol matrix=580.

Step E

The product obtained in step D was dissolved in MeOH, then 10% Pd/C (5% by weight with respect to the substrate) was added; the dispersion was hydrogenated (60 psi) at room temperature for 18 hours. At the end, the dispersion was filtered through celite and concentrated to dryness. The title product was obtained without further purifications.

Yield=99%. TLC silica gel $CHCl_3$:iPrOH:MeOH:$H_2O$:$CH_3COOH$ (42:7:28:10.5:10.5)/ acetone 8:2; Rf=0.57. $^1$H-NMR (300 MHz; $D_2O$): δ: 5.5–5.3 (m, 1H), 4.2–4.1 (m, 2H), 4.0–3.4 (m, 8H), 2.2–1.7 (m, 9H), 1.60–1.40 (m, 2H), 1.3–1.1 (m, 22H), 0.9–0.7 (t, 3H). Elemental analysis: responding to the expected formula $C_{25}H_{48}NO_6P$. MS-FAB+glycerol matrix=490. K.F.=7% water HPLC: Spherisorb-Cl (5 μm, 250×4.6 mm), mobile phase 0.075 M $KH_2PO_4$:$CH_3CN$ 60:40, flow 0.75 ml/min, detector: RI, UV 205 nm, RT=16.53 min.

EXAMPLE 13

R,S-3-trimethylammonium-2-(nonylaminocarbonyl)-oxy-1-propanephosphonate monobasic (ST 1286)

Step A

The product was prepared as disclosed in step A of Example 12.

Step C

The product obtained in the previous step (4 g, 10 mmoles) was dissolved in $CH_2Cl_2$ (10% solution) and etherated $BF_3$ (1.6 ml) and nonyl isocyanate (3.38 g, 20 mmoles) were added at room temperature. The reaction was worked up after 30 minutes, firstly adding further $CH_2Cl_2$, then washing the organic phase with 1N NaOH. several times. The product was purified on silica gel flash-chromatography (Hexane/AcOEt 7:3).

Yield=85%. TLC silica gel AcOEt/Hexane 6:4; Rf=0.28. $^1$H-NMR (300 MHz; $CDCl_3$): δ: 7.4–7.2 (m, 10H), 5.1–4.9. (m, 5H), 4.6–4.2 (m, 1H), 3.7–3.5 (dd, 2H), 3.2–3.0 (m, 2H), 2.4–2.2 (m, 2H), 1.5–1.3 (m, 2H), 1.3–1.1 (m, 12H), 0.9–0.7 (t, 3H). Elemental analysis: responding to the expected formula $C_{27}H_{40}BrNO_5P$.

Step F

The compound obtained in the preceding step (5.68 g, 10 mmoles) was dissolved in DMF (11 ml), together with TBAI (tetrabutyl ammonium iodide) in catalytic amounts (1% w/w with respect to the substrate). This solution was saturated with gaseous trimethylamine. The reaction was carried out at 50° C., until the starting compound disappeared. At the end of the reaction, the solution was high vacuum-concentrated, obtaining a semisolid, containing the product. The latter was isolated and purified through silica gel flash-chromatography using a gradient from $CH_2Cl_2$ only to $CH_2Cl_2$:MeOH 1.1. The product was obtained.

Yield: 25%. TLC silica gel $CHCl_3$:iPrOH:MeOH:$H_2O$:$CH_3COOH$ (42:7:28:10.5:10.5)/acetone 8:2; Rf=0.73. $^1$H-NMR (300 MHz; $CDCl_3$): δ: 7.5–7.2 (m, 5H), 5.5–5.4 (m, 1H), 4.9–4.8 (m, 4H), 4.0–3.6 (m, 2H), 3.2–3.1 (s, 9H), 2.2–2.1 (s, 9H), 2.0–1.8 (m, 2H), 1.5–1.4 (m, 2H), 1.4–1.2 (m, 12H), 0.9–0.7 (t, 3H). Elemental analysis: responding to the expected formula $C_{27}H_{42}N_2O_5P$. MS-FAB+glycerol matrix=457.

Step G

The product obtained in step F was dissolved in MeOH, then 10% Pd/C (5% by weight with respect to the substrate) was added; the dispersion was hydrogenated (60 psi) at room temperature for 18 hours. At the end, the dispersion was filtered through celite and concentrated to dryness. The title product was obtained without further purifications.

Yield=99%. TLC silica gel $CHCl_3$:iPrOH:MeOH:$H_2O$:$CH_3COOH$ (42:7:28:10.5:10.5)/acetone 8:2; Rf=0.31. $^1$H-NMR (300 MHz; $D_2O$): δ: 5.6–5.5 (m, 1H), 4.1–3.5 (m, 2H), 3.2–3.1 (s, 9H), 3.1–3.0 (m, 2H), 2.2–1.7 (m, 2H), 1.5–1.4 (m, 2H), 1.4–1.2 (m, 12H), 0.9–0.7 (t, 3H). Elemental analysis: responding to the expected formula $C_{15}H_{35}N_2O_5P$. MS-FAB+glycerol matrix=367. K.F.=3% water. HPLC: Spherisorb-Cl (5 μm, 250×4.6 mm), mobile phase 0.05 M $(NH_4)H_2PO_4$:$CH_3CN$ 35:65, flow 0.75 ml/min, detector: RI, UV 205 nm, RT=7.31 min.

EXAMPLE 14

R,S-3-pyridinium-2-(nonylaminocarbonyl)-oxy-1-propanephosphonic acid chloride (ST 1268)

Step A

The product was prepared as disclosed in step A of Example 12.

Step C

The product was prepared as disclosed in step C of Example 13.

Step H

The compound obtained in the preceding step (5.68 g, 10 mmoles) was dissolved in anhydrous pyridine (50% solution), together with TBAI (tetrabutyl ammonium iodide) in catalytic amounts (1% w/w with respect to the substrate). The reaction was carried out at 50° C., until the starting compound disappeared. At the end of the reaction, the solution was high vacuum-concentrated, obtaining a semisolid, containing the product, which was isolated and purified through silica gel flash-chromatography using a gradient from $CH_2Cl_2$ only to $CH_2Cl_2$:MeOH from 9:1 to 1:1.

Yield: 20%. TLC sica gel $CHCl_3$:iPrOH:MeOH:$H_2O$:$CH_3COOH$ (42:7:28:10.5:10.5)/acetone 8:2; Rf=0.73. $^1$H-NMR (300 MHz; $CDCl_3$): δ: 9.4–9.3 (d, 2H), 8.2–8.1 (t, 1H), 7.9–7.8 (t, 2H), 7.3–7.1 (m, 5H), 5.3–5.1 (m, 3H), 4.9–4.8 (m, 2H), 3.0–2.9 (m, 2H), 2.2–1.6 (m, 2H), 1.4–1.2 (m, 2H), 1.3–1.1 (m, 12H), 0.9–0.7 (t, 3H). Elemental analysis: responding to the expected formula $C_{24}H_{38}N_2O_5P$. MS-FAB+glycerol matrix=477.

Step I

The product obtained in step H (4.76 g, 10 mmoles) was dissolved in 100 ml $CH_2Cl_2$ and 20 mmoles TMSI (trimethylsilyl iodide) were added to the resulting solution. After 30 minutes, the reaction was finished; 0.5 ml water were added to the mixture, which was concentrated to dryness. The final product was purified and isolated by RP-18 silica gel chromatography, using a gradient water/methanol 9:1 to methanol 100%. The solid was dissolved in water and passed through IRA 402 resin (Cl- activated). ST 1268 was obtained.

Yield=80%. M.p.=202–204° C. TLC silica gel $CHCl_3$:iPrOH:MeOH:$H_2O$:$CH_3COOH$ (42:7:28:10.5:10.5)/acetone 8:2; Rf=0.48. $^1$H-NMR (300 MHz; $D_2O$): δ: 9.4–9.3 (d, 2H), 8.2–8.1 (t, 1H), 7.9–7.8 (t, 2H), 5.5 . 5.4 (m, 1H), 5.2–4.8 (m, 2H), 3.0–2.9 (m, 2H), 2.2–2.0 (m, 2H), 1.4–1.1 (m, 14H), 0.9–0.7 (t, 3H). Elemental analysis: responding to the expected formula $C_{18}H_{32}N_2$ $ClO_5P$. MS-FAB+glycerol matrix=387. K.F.=6% water. HPLC: Spherisorb-Cl (5 μm, 250×4.6 mm), mobile phase 0.050 M $KH_2PO_4$:$CH_3CN$ 35:65, flow 0.75 ml/min, detector: RI, UV 205 nm, RT=5.61 min.

EXAMPLE 15

R-4-trimethylammonium-3-(tetradecylcarbamoyl)-amino Butyrate (ST 1326)

The product was prepared as disclosed in Example 1, starting from tetradecyl isocyanate and R-aminocarnitine, inner salt, except the crude product was obtained by precipitation with ethyl ether, from the reaction mixture, directly washed with ethyl ether and purified on a silica gel chromatographic column.

Yield 57%. M.p.: 160–162° C. $[\alpha]_{20}^{D}$=−21.1° (c=0.5, MeOH). $^1$H-NMR (300 MHz; $CD_3OD$): δ: 4.52 1H). 3.60 (dd, 1H), 3.48 (d, 1H), 3.20 (s, 9H), 3.10 (t, 2H), 2.40 (m, 2H), 1.45 (m, 2H), 1.28 (brs, 22H), 0.8 (brt, 3H). ESI Mass=400, $[(M+H)^+$. Elemental analysis: responding to the expected formula $C_{22}H_{45}N_3O_3$. K.F.=2.5% water. TLC silica gel $CHCl_3$:iPrOH:MeOH:$H_2O$:$CH_3COOH$ 42:7:28:10.5: 10.5; Rf=0.50. HPLC; SGE-SCX column (5 μm, 250×4 mm), T=30° C., mobile phase 0.05 M $(NH_4)H_2PO_4$:$CH_3CN$ 75:25, pH=4.9 (as such), flow 0.75 ml/min, detector: RI, UV 205 nm, RT=13.63 min.

EXAMPLE 16

R-4-trimethylammonium-3-(undecylcarbamoyl)-aminobutyrate (ST 1327)

The product was prepared as disclosed in Example 1, starting from undecyl isocyanate and R-aminocarnitine, inner salt, purified on a silica gel chromatographic column and further purified by precipitation from acetonitrile.

Yield 50%. M.p.: 1.49–150.2° C. $[\alpha]_{20}^{D}$=−21.16° (c=1, MeOH). $^1$H-NMR (300 MHz; $CD_3OD$): δ: 4.52 1H), 3.60 (dd, 1H), 3.48 (d, 1H), 3.20 (s, 9H), 3.10 (t, 2H), 2.40 (m, 2H), 1.45 (m, 2H), 1.28 (brs, 16H), 0.8 (brt, 3H). ESI Mass=358, $[(M+H)^+$; Elemental analysis: responding to the expected formula $C_{19}H_{39}N_3O_3$. K.F.=2.3% water. TLC silica gel $CHCl_3$:iPrOH:MeOH:$H_2O$:$CH_3COOH$ 42:7:28:10.5: 10.5. Rf=0.50. HPLC: SGE-SCX column (5 μm, 250×4 mm), T=30° C., mobile phase 0.05 M $(NH_4)H_2PO_4$:$CH_3CN$ 80:20, pH=4.9 (as such), flow 0.75 ml/min, detector: RI, UV 205 nm, RT=17.37 min.

EXAMPLE 17

R-4-trimethylammonium-3-(heptylcarbamoyl)-aminobutyrate (ST 1328)

The product was prepared as disclosed in Example 1, starting from heptyl isocyanate and R-aminocarnitine, inner salt, purified on a silica gel chromatographic column and further purified by precipitation from acetonitrile.

Yield 47%. M.p.: 149–150° C. $[\alpha]_{20}^{D}$=−34.0° (c=0.97, MeOH). $^1$H-NMR (300 MHz; $CD_3OD$): δ: 4.52 (m, 1H), 3.60 (dd, 1H), 3.48 (d, 1H), 3.20 (s, 9H), 3.10 (t, 2H), 2.40 (m, 2H), 1.45 (m, 2H), 1.30 (brs, 8H), 0.8 (brt, 3H). ESI Mass=302, $[(M+H)^+$; Elemental analysis: responding to the expected formula $C_{15}H_{31}N_3O_3$K.F.=6.17% water TLC silica gel $CHCl_3$:iPrOH:MeOH:$H_2O$:$CH_3COOH$ 42:7:28:10.5:10.5. Rf=0.50. HPLC: SGE-SCX column (5 μ, 250×4 mm), T=30° C., mobile phase 0.05 M $(NH_4)H_2PO_4$:$CH_3CN$ 85:15, pH=6 ($H_3PO_4$), flow 0.75 ml/min, detector: RI, UV 205 nm, RT=7.16 min.

EXAMPLE 18

R,S-4-trimethylammonium-3-(nonylthiocarbamoyl)-aminobutyrate (ST 1329)

The product was prepared as disclosed in Example 1, starting from nonyl isothiocyanate and R,S-aminocarnitine, inner salt. Chromatography was carried out with a $CHCl_3$/MeOH gradient from 8:2 to 2:8.

Yield 53% M.p.: 104–107° C. $^1$H-NMR (200 MHz; $CD_3OD$): δ: 5.45 (brm, 1H), 3.75 (dd, 1H), 3.55 (d, 1H), 3.45 (brm, (2H), 3.22 (s, 9H), 2.48 (m, 2H), 1.55 (m, 2H), 1.30 (brs,-12H), 0.90 (brt, 3H). ESI Mass=346, $[(M+H)^+$; Elemental analysis: responding to the expected formula $C_{17}H_{35}N_3O_2S$ K.F.=2.6% water; TLC silica gel $CHCl_3$:iPrOH:MeOH:$H_2O$:$CH_3COOH$ 42:7:28:10.5:10.5. Rf=0.74; HPLC: SGE-SCX column (5 μm, 250×4 mm), T=30° C., mobile phase 0.05 M $(NH_4)H_2PO_4$:$CH_3CN$ 85:15, pH=6.0 ($H_3PO_4$), flow 0.75 ml/min, detector: RI, UV 205 nm, RT=8.87 min.

EXAMPLE 19

R-4-trimethylammonium-3-(nonylcarbamoyl)-aminobutyrate (ST 1283)

The product was prepared as disclosed in Example 1, starting from nonyl isocyanate and R-aminocarnitine, inner salt. M.p.: 146–147° C. $[\alpha]_{20}^{D}$=−13.4° (c=0.5, $H_2O$). Elemental analysis: responding to the expected formula $C_{17}H_{35}N_3O_3$ K.F.=2.8% water. Remaining physico-chemical data were coincident with those of racemic ST1251 (Example 1).

EXAMPLE 20

S-4-trimethylammonium-3-(nonylcarbamoyl)-aminobutyrate (ST 1338)

The product was prepared as disclosed in Example 1, starting from nonyl isocyanate and S-aminocarnitine, inner salt.

M.p.: 146–147° C. $[\alpha]_{20}^{D}$=+16.7° (c=0.43, $H_2O$). $^1$H-NMR (300 MHz; $CD_3OD$): δ: 4.52 (m, 1H), 3.60 (dd, 1H), 3.45 (d, 1H), 3.18 (s, 9H), 3.10 (t, 2H), 2.40 (m, 2H), 1.45 (m, 2H), 1.28 (brs, 12H), 0.90 (brt, 3H). ESI Mass=330, $[(M+H)^+$; Elemental analysis: responding to the expected formula $C_{17}H_{35}N_3O_3$ K.F.=1.8% water. Remaining physico-chemical data were coincident with those of racemic ST1251 (Example 1).

EXAMPLE 21

S-4-trimethylammonium-3-(tetradecylcarbamoyl)-aminobutyrate (ST 1340)

The product was prepared as disclosed in Example 1, starting from tetradecyl isocyanate and S-aminocarnitine, inner salt, except the crude product was obtained by precipitation with ethyl ether, from the reaction mixture, directly washed with ethyl ether and purified on a silica gel chromatographic column.

Yield=57%; M.p.: 166–167° C. $[\alpha]_{20}^{D}$=+20.7° (c=0.5, MeOH). Elemental analysis: responding to the expected formula $C_{22}H_{45}N_3O_3$ K.F. =1.7% water. Remaining physico-chemical data were coincident with those of racemic ST1326 (Example 15).

EXAMPLE 22

Isobutyl R,S-4-trimethylammonium-3-tetradecylamino-aminobutyrate (ST 1252)

R,S-4-trimethylammonium-3-tetradecylamino-aminobutyrate is isobutyl Ester Acetate Isobutyl ester of racemic aminocarnitine (5 g, 0.0198 moles) and tetradecanal (4.6 g, 0.0217 moles) were dissolved into 250 ml methanol. Glacial acetic acid (1.13 ml, 0.198 moles) and 1 g 10% Pd/C were added. The mixture was hydrogenated at 30 psi overnight. After filtration on celite, the solution was vacuum-concentrated. A pale yellow oil was obtained, which was purified through a silica gel column, eluting firstly with AcOEt, then AcOEt/MeOH 9:1. 4 g of product were obtained.

Yield=47%;

TLC silica gel ($CHCl_3$ 42/MeOH 28/isopropyl alcohol 7/water 10.5/acetic acid 10.5)/methyl acetate 7:3

Rf=0.74. $^1$H-NMR (300 MHz; $CD_3OD$): δ: 3.92–3.90 (d, 2H), 3.64–3.58 (m, 1H), 3.50–3.30 (m, 2H), 2.80–2.50 (m, 4H), 2.0–1.9 (m, 1H), 2.6–2.4 (m, 2H), 1.3 (s, 22H), 0.98–0.82 (m, 9H).

R,S-4-trimethylammonium-3-tetradecylamino-aminobutyrate

The isobutyl ester of R,S-4-trimethylammonium-3-tetradecylamino-aminobutyric acid, acetate salt, (3.3 g) was hydrolysed on Amberlyst IRA 402 resin ($OH^-$ activated form) and eluted with water. Water was evaporated to dryness under reduced pressure; the resulting white solid was washed with methanol, filtered and vacuum-dried. 1.95 g of product were obtained.

Yield 70% M.p.=160° C. dec. $^1$H-NMR (300 MHz; $CD_3OD$): δ: 4.4 (m, 1H), 3.40–3.35 (m, 3H), 3.2 (s, 9H), 2.80–2.72 (m, 1H), 2.56–2.42 (m, 2H), 2.27–2.16 (m, 1H), 1.55–1.40 (m, 2H), 1.3 (s, 22H), 0.92–0.85 (t, 3H). Elemental analysis: responding to the expected formula $C_{21}H_{44}N_2O_2$ K.F.=1.93 % water. TLC silica gel ($CHCl_3$ 42/MeOH 28/isopropyl alcohol 7/water 10.5/acetic acid 10.5) Rf=0.5. HPLC: SGE-SCX column (5 μm, 250×4 mm), mobile phase 0.05M $(NH_4)H_2PO_4$:$CH_3CN$ 60:40, pH=4, flow=0.75 ml/min; detector: RI, UV 205 nm, RT=30.017 min.

EXAMPLE 23

R,S-4-trimethylammonium-3-octylaminobutyrate (ST 1254)

R,S-4-trimethylammonium-3-octylamino-aminobutyrate Isobutyl Ester Acetate

Isobutyl ester of racemic aminocarnitine chloride, (5 g, 0.0198 moles) and octanaldehyde (2.79 g, 0.0217 moles) were dissolved into 250 ml methanol. Glacial acetic acid (1.13 ml, 0.198 moles) and 1 g 10% Pd/C were added. The mixture was hydrogenated at 30 psi overnight. After filtration on celite, the solution was vacuum-concentrated. 8.5 g product were obtained, subsequently purified through a silica gel column, eluting firstly with AcOEt, then AcOEt/MeOH (9:1; 8.5:1.5). 3 g of product were obtained.

Yield=40%; TLC silica gel ($CHCl_3$ 42/MeOH 28/isopropyl alcohol 7/water 10.5/acetic acid 10.5) Rf=0.54. $^1$H-NMR (300 MHz; $CD_3OD$): δ: 3.92–3.90 (d, 2H), 3.64–3.58 (m, 1H), 3.50–3.30 (m, 2H), 2.80–2.50 (m, 4H), 2.0–1.9 (m, 1H), 2.6–2.4 (m, 2H), 1.3 (s, 10H), 0.98–0.82 (m, 9H).

R,S-4-trimethylammonium-3-octylaminobutyrate

The isobutyl ester of R,S-4-trimethylammonium-3-tetradecylamino-aminobutyric acid, acetate salt, (2.8 g, 0.00719) was hydrolysed on Amberlyst IRA 402 resin ($OH^-$ activated form) and eluted with water. Water was evaporated to dryness under reduced pressure; the resulting white solid was washed with methanol, filtered and vacuum-dried. 1.8 g of product were obtained.

Yield 70% M.p.=140° C. dec. $^1$H-NMR (300 MHz; $CD_3OD$): δ: 3.42–3.30 (m, 3H), 3.2 (s, 9H), 2.85–2.70 (m, 1H), 2.60–2.40 (m, 2H), 2.30–2.20 (m, 1H), 1.55–1.40 (m, 2H), 1.3 (s, 10H), 0.92–0.85 (t, 3H). Elemental analysis: responding to the expected formula $C_{15}H_{32}N_2O_2$ K.F.=2.8 % water. TLC silica gel ($CHCl_3$ 42/MeOH 28/isopropyl alcohol 7/water 10.5/acetic acid 10.5) Rf=0.32. HPLC: SGE-SCX column (5 μm, 250×4 mm), mobile phase 0.05M $(NH_4)H_2PO_4$: $CH_3CN$ 40:60, pH=4, flow=0.75 ml/min; detector: RI, UV 205 nm, RT=43.20 min.

EXAMPLE 24

R,S-4-trimethylammonium-3-(decansulfonyl) aminobutyrate (ST 1364)

Aminocarnitine isobutyl ester chloride hydrochloride

Isobutyl ester of aminocarnitine, inner salt (3 g, 18.72 mmoles), was dissolved in isobutanol (120 ml) and ice-bath cooled. Gaseous HCl was bubbled into the solution until complete saturation and clearing of the mixture. The solution was refluxed (bath temperature 130° C.) overnight. The solvent was vacuum-evaporated and the residue was triturated with $Et_2O$. 5.1 g of white solid were obtained.

Yield=95%; $^1$H-NMR (200 MHz; $D_2O$): δ: 4.3 (m, 1H), 4.0 (d, 2H), 3.8 (d, 2H), 3.2 (s, 9H), 3.1 (m, 2H), 2.0 (m, 1H), 0.9 (d, 6H). Elemental analysis: responding to the expected formula $C_{11}H_{26}C_2N_2O_2$. K.F.=1 % water.

R,S-4-trimethylammonium-3-(decansulfonyl)-aminobutyrate

The isobutyl ester of R,S-aminocarnitine chloride, hydrochloride (1 g, 3.46 mmoles) in anhydrous dichloromethane (5 ml) was added with triethylamine (2.65 ml, 19mmoles) and decansulfonyl chloride (2.1 g, 8.65 mmoles) -suspended in 3 ml anhydrous dichloromethane, at 0° C. The mixture was left under stirring for 3 days at room temperature. The solvent was evaporated to dryness, the residue was taken up with ethyl acetate and the white precipitate of triethylamine hydrochloride was separated by from the solution by vacuum-filtration. The ethyl acetate solution was vacuum-dried to give 2.8 g of a yellow oil. 71 ml 1N NaOH were added to hydrolize the isobutyl ester, leaving the suspension under stirring overnight at room temperature. The suspension was evaporated and vacuum-dried, and the solid residue was completely dried under oil-vacuum, taken up with methanol and purified through silica gel chromatographic column, using methanol as eluant. 555 mg of product were obtained.

Yield 44% M.p=158° C. dec. $^1$H-NMR (300 MHz; $CD_3OD$): δ: 4.3 (m, 1H), 3.45 (m, 2H), 3.25 (s, 9H), 3.15 (m, 2H), 2.45 (d, 2H), 1.8 (m, 2H), 1.45 (m, 2H), 1.4 (brs, 12H), 0.9 (brt, 3H). Elemental analysis: responding to the expected formula $C_{17}H_{36}N_2O_4S$ Mass ESI=365 [$(M+H)^+$], 387[$(M+Na)^+$] K.F.=3% water. TLC silica gel ($CHCl_3$ 42/MeOH 28/isopropyl alcohol 7/water 10.5/acetic acid 10.5) Rf=0.62. HPLC: Spherisorb-Cl column (5 μm, 250×4.6 mm), mobile phase 0.05M $K_2H_2PO_4$:$CH_3CN$ 35:65, pH as such, flow=0.73 ml/min; temperature=30° C., detector: RI, UV 205 nm, RT=7.0 min.

EXAMPLE 25

R,S-4-trimethylammonium-3-(nonylsulfamoyl) aminobutyrate (ST 1362)

The isobutyl ester of R,S-aminocarnitine chloride, hydrochloride (2 g, 6.9 mmoles) in anhydrous dichloromethane (40 ml) was added with triethylamine (3.8 ml, 27.6 mmoles) and dropped with $SO_2Cl_2$ in dichloromethane (1.7 ml in 10 ml final solution) at 0° C. The mixture was left under stirring for 3 days at room temperature, triethylamine (1.9 ml, 13.8 mmoles) and nonylamine (2.5 ml, 13.8 mmoles) were added and the reaction mixture was left under stirring overnight at room temperature. The solvent was vacuum-evaporated, the residue was taken up with ethyl acetate (100 ml) and the precipitate of triethylamine hydrochloride was separated from the solution by vacuum-filtration. The ethyl acetate solution was vacuum-dried to give 4.8 g of a yellow oil, to which were added 105 ml 1N NaOH to hydrolize the isobutyl ester. The mixture was left under stirring overnight at room temperature and vacuum-dried. The residue was completely dried under oil-vacuum. The yellow semisolid was crystallized from chloroform. 1.26 g of product were obtained.

Yield 50% M.p.=152° C. dec. $^1$H-NMR (300 MHz; $CD_3OD$): δ: 4.1 (m, 1H), 3.48 (d, 2H), 3.25 (s, 9H), 2.95 (m, 2H), 2.5 (t, 2H), 1.55 (t, 2H), 1.45 (brs, 12H), 0.9 (brt, 3H).

Elemental analysis: responding to the expected formula $C_{16}H_{35}N_3O_4S$ Mass ESI=366 [(M+H)$^+$], 388[(M+Na)$^+$] K.F.=5.8% water. TLC silica gel ($CHCl_3$ 42/MeOH 28/isopropyl alcohol 7/water 10.5/acetic acid 10.5) Rf=0.34. HPLC: Spherisorb-Cl column (5 μm, 250×4.6 mm), mobile phase 0.05M $KH_2PO_4$:$CH_3CN$ 35:65, pH as such, flow=0.75 ml/min; temperature=30° C., detector: RI, UV 205 nm, RT=6.68 min.

EXAMPLE 26

S-4-trim ethylammonium-3-(dodecansulfonyl) aminobutyrate (ST 1391)

The product was prepared as disclosed in Example 24, starting from isobutyl ester of S-aminocarnitine chloride, hydrochloride and dodecansulfonyl chloride, to give 600 mg of product.

Yield 44% M.p.=156° C. dec. $[\alpha]_D^{20}$=+6° (c=0.245%, $H_2O$) $^1$H-NMR (300 MHz; $CD_3OD$): δ: 4.3 (m, 1H), 3.45 (m, 2H), 3.25 (s, 9H), 3.15 (m, 2H), 2.45 (d, 2H), 1.8 (m, 2H), 1.45 (m, 2H), 1.4 (brs, 16H), 0.9 (brt, 3H). Elemental analysis: responding to the expected formula $C_{19}H_{40}N_2O_4S$ K.F.=8.6% water. TLC silica gel ($CHCl_3$ 42/MeOH 28/isopropyl alcohol 7/water 10.5/acetic acid 10.5) Rf=0.65. HPLC: Spherisorb-Cl column (5 1 μm, 250×4.6 mm), mobile phase 0.05M $KH_2PO_4$:$CH_3CN$ 40:60, pH as such, flow=0.75 ml/min; temperature=30° C., detector: RI, UV 205 nm, RT=8.5 min.

EXAMPLE 27

R-4-trimethylammonium-3-(dodecansulfonyl) aminobutyrate (ST 1420)

The product was prepared as disclosed in Example 24, starting from isobutyl ester of R-aminocarnitine chloride, hydrochloride and dodecansulfonyl chloride, to give 450 mg of product.

Yield 34% M.p.=158° C. dec. $[\alpha]_D^{20}$=−7° (c=0.265%, $H_2O$) $^1$H-NMR (300 MHz; $CD_3OD$): δ: 4.3 (m, 1H), 3.45 (m, 2H), 3.28 (s, 9H), 3.15 (m, 2H), 2.45 (d, 2H), 1.8. (m, 2H), 1.45 (m, 2H), 1.3 (brs, 16H), 0.9 (brt, 3H). Elemental analysis: responding to the expected formula $C_{19}H_{40}N_2O_4S$ K.F.=6.9% water. TLC silica gel ($CHCl_3$ 42/MeOH 28/isopropyl alcohol 7/water 10.5/acetic acid 10.5) Rf=0.66. HPLC: Spherisorb-Cl column (5 μm, 250×4.6 mm), mobile phase 0.05M $KH_2PO_4$:$CH_3CN$ 40:60, pH as such, flow=0.75 ml/min; temperature=30° C., detector: RI, UV 205 nm, RT=8.11 min.

EXAMPLE 28

S-4-trimethylammonium-3-(undecylsulfamoyl) aminobutyrate (ST 1427)

The product was prepared as disclosed in Example 25, starting from isobutyl ester of S-aminocarnitine chloride, hydrochloride and undecyl amine, except the crude product was purified on a silica gel chromatographic column, using a gradient $CHCl_3$: MeOH 9:1 to 1:9. The product was further purified on a silica gel chromatographic column, using MeOH. 0.7 g of pure product were obtained.

Yield 38% M.p.=153° C. dec. $[\alpha]_D^{20}$=+4° (c=0.25%, $H_2O$, pH=2) $^1$H-NMR (300 MHz; $CD_3OD$): δ: 4.1 (m, 1H), 3.48 (d, 2H), 3.25 (s, 9H), 2.95 (m, 2H), 2.5 (m, 2H), 1.55 (brt, 2H), 1.45 (brs, 16H), 0.9 (brt, 3H). Elemental analysis: responding to the expected formula $C_{18}H_{39}N_3O_4S$ K.F.=2.9% water. TLC silica gel ($CHCl_3$ 42/MeOH 28/isopropyl alcohol 7/water 10.5/acetic acid 10.5) Rf=0.68. HPLC: Spherisorb-Cl column (5 μm, 250×4.6 mm), mobile phase 0.05M $KH_2PO_4$:$CH_3CN$ 60:40, pH as such, flow=0.7 ml/min; temperature=30° C., detector: RI, UV 205 nm, RT=8.384 min.

EXAMPLE 29

R-4-trimethylammonium-3-(undecylsulfamoyl) aminobutyrate (ST 1428)

The product was prepared as disclosed in Example 25, starting from isobutyl ester of S-aminocarnitine chloride, hydrochloride and undecyl amine, except the crude product was purified on a silica gel chromatographic column, using a gradient $CHCl_3$: MeOH 9:1 to 1:9. The product was further purified on a silica gel chromatographic column, using MeOH. 0.5 g of product were obtained.

Yield 32% M.p.=158° C. dec. $[\alpha]_D^{20}$=−4° (c=0.25%, $H_2O$, pH=2) $^1$H-NMR (300 MHz; $CD_3OD$): δ: 4.1 (m, 1H), 3.48 (d, 2H), 3.25 (s, 9 H), 2.95 (m, 2H), 2.5 (m, 2H), 1.55 (brm, 2H), 1.45 (brs, 16H), 0.9 (brt, 3H). Elemental analysis: responding to the expected formula $C_{18}H_{39}N_3O_4S$ K.F.=4.77% water. TLC silica gel ($CHCl_3$ 42/MeOH 28/isopropyl alcohol 7/water 10.5/acetic acid 10.5) Rf=0.68. HPLC: Spherisorb-Cl column (5 μm, 250×4.6 mm), mobile phase 0.05M $KH_2PO_4$:$CH_3CN$ 60:40, pH as such, flow=0.7 ml/min; temperature=30° C., detector: RI, UV 205 nm, RT=8.379 min.

EXAMPLE 30

R-4-trimethylammonium-3-(dodecylcarbamoyl) aminobutyrate (ST 1375)

The product was prepared as disclosed in Example 1, starting from R-aminocarnitine inner salt and dodecylisocyanate. The crude product obtained after washing with diethyl ether was purified on a silica gel chromatographic column to give 4.8 g of product.

Yield 55% M.p.=147° C. dec. $[\alpha]_D^{20}$=−24.6° (c=0.48%, MeOH) $^1$H-NMR (300 MHz; $CD_3OD$): δ: 4.51 (m, 1H), 3.60 (dd, 1H), 3.45 (dd, 1H), 3.2 (s, 9H), 3.1 (t, 2H), 2.4 (m, 2H), 1.45 (m, 2H), 1.3 (brs, 18H), 0.9 (t, 3H). Elemental analysis: responding to the expected formula $C_{20}H_{41}N_3O_3$ K.F.=5.4% water. TLC silica gel ($CHCl_3$ 42/MeOH 28/isopropyl alcohol 7/water 10.5/acetic acid 10.5) Rf=0.6. HPLC: Spherisorb-Cl column (5 μm, 250×4.6 mm), mobile phase 0.05M $KH_2PO_4$:$CH_3CN$ 65:35, pH=5.6, flow=0.75 ml/min; temperature=30° C., detector: RI, UV 205 nm, RT=8.5 min.

EXAMPLE 31

R-4-trimethylammonium-3-(10-phenoxydecylcarbamoyl)aminobutyrate (ST 1449)

10-Phenoxydecyl Isocyanate

A solution of 11-phenoxyundecanoyl chloride (31.1 g, 104.8 mmoles) in acetone (30 ml) was dropped into a solution of sodium azide (9.53 g, 146.6 mmoles) in water (30 ml), cooled in an ice bath, keeping the solution temperature between 10 and 15° C. After one hour, the solution was transferred in a separatory funnel and the lower phase (the aqueous one) was eliminated. The higher phase was transferred into a flask containing 100 ml of toluene, previously warmed at 65° C. After 1.5 hours, the solution was evaporated to dryness, giving 13.37 g of crude product, which could be used as such in the subsequent reaction.

$^1$H-NMR (300 MHz; $CDCl_3$): δ: 7.2 (m, 2H), 6.9 (m, 3H), 3.9 (t, 2H), 3.6 (t, 2H), 1.4 (m, 2H), 1.3 (m, 10H).

R-4- trimethylammonium-3-(10 -phenoxydecylcarbamoyl)-amino Butyrate 10-phenoxydecylisocyanate (25.0 g, 91.12 mmoles) was added to a solution of aminocarnitine, inner salt (7.3 g, 45.56 mmoles) in anhydrous DMSO (350 ml) and the solution was left to stand for 60 hours at 40° C. The resulting mixture was transferred in a 3 l Erlenmeyer flask containing ethyl ether (2.5 l) and the solvent was separated by decantation of the formed precipitate, which was then taken with few chloroform, transferred into a flask and precipitated again with ethyl ether. The so obtained crude product was washed several times with ethyl ether and purified on a silica gel chromatographic column, using a gradient $CHCl_3$: MeOH 9:1 to $CHCl_3$: MeOH 3:7 gradient until elution of impurities with higher Rf, then eluting the product of interest with MeOH only. 13.5 g of pure product were obtained.

Yield 68% $^1$H-NMR (300 MHz; $CD_3OD$): δ: 7.2 (m, 2H), 6.9 (m, 3H), 4.5 (m, 1H), 3.9 (t, 2H), 3.6 (dd, 1H), 3.4 (dd, 1H), 3.2 (s, 9H), 3.1 (t, 2H), 2.4 (m, 2H), 1.8 (m, 2H), 1.6 (m, 2H), 1.4 (m, 2H), 1.3 (m, 10H). FAB Mass=436, $[(M+H)^+]$; Elemental analysis: responding to the expected formula $C_{24}H_{41}N_3O_4$ K.F.≦2.3% water.

EXAMPLE 32

R-4-trimethylammonium-3-(trans-β-styrenesulfonyl) aminobutyrate (ST 1448)

R-aminocarnitine isobutyl ester chloride hydrochloride

R-aminocarnitine inner salt (3 g, 18.72 mmoles) was dissolved in isobutanol (120 ml) and ice-bath cooled. Gaseous HCl was bubbled into the solution until complete saturation and clearing of the mixture. The solution was refluxed (bath temperature 130° C.) overnight. The solvent was vacuum-evaporated and the residue was triturated with $Et_2O$. 5.1 g of white solid were obtained.

Yield=95%; $^1$H-NMR (200 MHz; $D_2O$): δ: 4.3 (m, 1H), 4.0 (d, 2H), 3.8 (d, 2H), 3.2 (s, 9H), 3.1 (m, 2H), 2.0 (m, 1H), 0.9 (d, 6H). Elemental analysis: responding to the expected formula $C_{11}H_{26}Cl_2N_2O_2$. K.F.=1% water.

R-4-trimethylammonium-3-(trans-β-styrenesulfonyl)-aminobutyrate

The isobutyl ester of R-aminocarnitine chloride, hydrochloride (1 g, 3.46 mmoles) in anhydrous dichloromethane (5 ml) was added with triethylamine (2.65 ml, 19 mmoles) and trans-β-styrenesulfonyl chloride (1.753 g, 8.65 mmoles) suspended in 3 ml anhydrous dichloromethane, at 0° C. The mixture was left under stirring for 3 days at room temperature. The solvent was evaporated to dryness, the residue was taken up with ethyl acetate (100 ml) and the white precipitate of triethylamine hydrochloride was separated by from the solution by vacuum-filtration. The ethyl acetate solution was vacuum-dried, then 71 ml 1N NaOH were added to hydrolize the isobutyl ester, leaving the suspension under stirring overnight at room temperature. The suspension was evaporated and vacuum-dried, and the solid residue was completely dried under oil-vacuum, taken up with methanol and purified through silica gel chromatographic column, using methanol as eluant. 565 mg of product were obtained.

Yield 50% $^1$H-NMR (300 MHz; $CD_3OD$): δ: 7.8 (d, 1H), 7.5 (m, 5H), 7.3 (d, 1H), 4.3 (m, 1H), 3.4 (m, 2H), 3.2 (s, 9H), 2.4 (d, 2H). Elemental analysis: responding to the expected formula $C_{15}H_{22}N_2O_4S$ ESI Mass=327 $[(M+H)^+]$

PHARMACOLOGICAL ACTIVITY

Determination of CPT Inhibiting Activity.

CPT inhibition was evaluated essentially as described in Kerner, J. & Bieber, L. L. (1990) Biochemistry 29: 4326–34 on fresh mitochondrial preparations obtained from normally fed Fischer rat liver or heart. Mitochondria were isolated from liver or heart and suspended in 75 mM saccharose buffer, 1 mM EGTA, pH 7.5. 100 μl mitochondrial suspension, containing 50 μM [$^{14}$C] palmitoyl-CoA (specific activity 10,000 DPM/mole) and 10 mM L-carnitine, were incubated at 37° C., in the presence of scalar concentrations of the test product (0–3 mM). Reaction time: 1 minute.

Table 1 shows the $IC_{50}$ determined.

The compounds of the present invention have higher inhibiting activity than the one of the reference compound SDZ-CPI-975, Example 1, disclosed in EP 0 574 355.

TABLE 1

$IC_{50}$ of inhibition CPTI curve in rat liver mitochondrin

| Compound | $IC_{50}$ (μM/l) |
|---|---|
| SDZ-CPI-975 | 17.4 |
| ST1326 | 0.75 |
| ST1327 | 3.2 |

Determination of oleate-stimulated β-hydroxybutyrate production

β-hydroxybutyrate production is an index of CPT activity. In fact, the production of ketone bodies, final products of mitochondrial β-oxidation, is related to CPT activity.

Mitocondrial preparations, obtained according to the method by Venerando et al. (Am J. Physiol. 266:C455–C461, 1994), were used. Hepatocytes are incubated at 37° C. in KRB bicarbonate buffer at pH 7.4, 6 mM glucose, 1% BSA in $O_2/CO_2$ 95/5 atmosphere at $2.5\times10^5$ cells/ml. After 40 min incubation with the test compound at different concentrations, the first set of samples was taken ($T_{0\ min}$) and oleate was added (1 mM final in KRB+BSA 1.4%). After 20 minutes, the second withdrawal was made ($T_{20\ min}$).

Table 2 shows the results. The data are the mean of three different experiments, twice carried out.

The compounds of the present invention have higher β-hydroxybutyrate inhibiting activity than the one of the reference compound SDZ-CPI-975, Example 1, disclosed in EP 0 574 355.

TABLE 2

$IC_{50}$ of inhibition CPTI curve of β-hydroxybutyrate production in rat hepatocytes

| Compound | $IC_{50}$ (μM/l) |
|---|---|
| SDZ-CPI-975 | 3.7 |
| ST1251 | 0.5 |
| ST1253 | 0.9 |
| ST1285 | 1.9 |

Glucose and β-hydroxybutyrate in Serum Fasted Rats Treated With CPT Inhibitors

Normally fed Fischer rats were starved for 24 hours and subsequently treated with the test compounds. One hour after the treatment, the animals were sacrificed and serum concentrations of glucose and β-hydroxybutyrate were determined.

Table 3 shows the results. For the compound ST1326 were used doses of 14.5 mg/2 ml/kg, for other test compounds, the doses are equivalent to ST1326 one.

TABLE 3

β-hydroxybutyrate and glucose serum concentration in 24 hours-starved rats, after one hour from intraperitoneal treatment.

| | control | SDZ CPI-975 | ST1251 | ST1253 | ST1326 | ST1327 | ST1328 |
|---|---|---|---|---|---|---|---|
| β-OHB | | | | | | | |
| Mean | 1867 | 119.9 | 99.8 | 118.8 | 133.1 | 93.0 | 169.2 |
| s.c. | 240 | 12.8 | 8.3 | 20.4 | 22.4 | 8.7 | 26.7 |
| p< | — | 0.001 | 0.001 | 0.001 | 0.001 | 0.001 | 0.001 |
| Glu | | | | | | | |
| Mean | 108.8 | 87.6 | 76.9 | 88.2 | 84.2 | 84.9 | 79.5 |
| s.c. | 6.7 | 1.0 | 2.3 | 3.9 | 2.4 | 1.6 | 1.6 |
| p< | — | 0.05 | 0.01 | 0.05 | 0.05 | 0.05 | 0.05 |

Glucose and Insulin Levels in Diabetic Animals Treated with CPT Inhibitors

C57BL/6J male rats, 5-weeks old, were provided by Ch. River. After 10 days of acclimatisation in standard conditions (22±2° C.; 55±15% humidity; 15–20/h air changes; 12 hours light-dark cycle, with 700–1900 lux) and with standard diet with 4RF21 feedstock (Mucedola), glycaemia was controlled in post-absorption state (starving from 8.30 a.m. to 4.30 p.m.). Blood withdrawal was carried out cutting the tail end. Glucose was analysed in blood acid supernatant (HCLO4 0,375 N) with autoanalyzer Cobas Mira S with Glucose GDH Kit (Roche).

The animals were divided in two groups, 26 mice each and fed with a high-fat and a low-fat diet, respectively.

After 2 months from the start of the diet, glycaemia was tested, according to the starting method. After about 3 months from the start of the diet, glycaemia was tested, according to the starting method and plasma insulin levels were also determined (with blood withdrawal from end tail cutting) using [125I] Rat Insulin Kit (Amersham).

One 10 mice group fed with low-fat diet and two 10-mice groups fed with high -fat diet were selected One of the two high fat diet was administered with ST 1327 at the dose of 45 mg/Kg in deionised H2O (p.o., twice a day, 8.30 a.m. and 5.30 p.m.).administration volume was 10 ml/Kg. the two remaining groups was treated with vehicle only. High-fat or low-fat diets were continued during the treatment.

After 20 days of treatment, glycaemia and plasma insulin were measured. After 43 days of treatment, the animals were sacrificed by decapitation in post-absorption state (fasting 8.30 a.m.–4.30 p.m.), 8 hours after the last treatment. Blood was withdrawn and serum was separated by centrifugation and stored at −80° C. Liver, heart and skeletal muscle (upper limbs) were also extracted, frozen in dry ice-acetone and kept at −80° C.

High-fat diet determined an increase of body weight, glycaemia and insulin, with respect to low-fat diet.

After 20 days of treatment with ST 1327, glucose and insulin levels significantly decreased.

Table 4 shows the results.

TABLE 4

Glucose and insulin levels in rats fed with fat-rich diet.

| Compound | High Fat diet Control | High Fat diet Treated | Low fat diet Control |
|---|---|---|---|
| Glucose mg/dl | 248.5 ± 11.03 (10) | 181.4 ± 9.63* (9) | 207.3 ± 6.84** (9) |
| Insulin ng/ml | 1.632 ± 0.246 (10) | 0.621 ± 0.117** (9) | 0.549 ± 0.050* (9) |

Student's t test, * and ** indicate p<0.001 and p<0.01, respectively, against high fat diet; ( ) indicates the number of cases.

These results shows that the compounds according to the present invention are effective in controlling glycaemia in fasting conditions. This is an important aspect in the treatment of diabetes, wherein hepatic gluconeogenesis occurs during fasting periods (i.e. nocturnal rest).

The effect of CPT Inhibitors on Myocardial Ischemia

The compounds of the present invention are also effective in the treatment of ischemia, in particular myocardial ischemia.

To this end, male Wistar rats, weighing 200–225 g, provided by Charles-River, were kept at constant temperature of 23°+/−1° C., 50+/−10% relative humidity, 12 hours light-dark cycle, fed with pellet 4RF2 1 (Mucedola) tap water ad libitum.

The animals were anaesthetised with sodium Pentobarbital at the dose of 70 mg/Kg i.p. Hearts were rapidly removed and put in a cold Krebs-Henseleit solution, before incannulation of aorta e subsequent perfusion according to Langendorff technique at 37° C. with a pressure of 100 cm water.

Perfusion medium (Krebs-Henseleit) at pH 7.4 consists in: 128 mM NaCl, 4.7 mM KCl, 1 mM MgCl2, 0.4 mM Na2HPO4, 20.2 mM NaHCO3, 1.3 mM CaCl2, 5 mM glucose. The medium was constantly oxygenated with carbogen (95% O2, 5% CO2).

After a 10 min "conditioning" period, hearts were perfused in a recirculant apparatus for 20 min. with the same medium containing 0.6 mM palmitate complexed with albumine (fraction V, fatty acid free), with or without the CPT inhibitor according to the present invention. By way of example ST 1364 was used at concentrations of 1 and 5 μM. After such a period ischemia was induced by reducing perfusion hydrostatic pressure from 100 cm to 20 cm for a period of 30 min. Reperfusion was started re-establishing the starting pressure conditions (100 cm). Hearts were controlled for 20 min. the inhibitor is present also during reperfusion phase.

Lactate dehydrogenases (LDH) release was monitored in the effluent in normal oxygenation conditions, during ischemia, with a withdrawal of medium at 30', and during reperfusion, with withdrawals at 1.5, 10, 15 and 20 minutes.

LDH release in the effluent is remarkably reduced, during reperfusion results significantly reduced in the presence of ST1364 at the dose of 5 μM (FIG. 1). This result indicates a lower entity of cellular damage from reperfusion of the treated with respect to the controls.

Statistical analysis was carried out with Student's "t" test for non-paired data.

The number of the cases for each group is six (n=6).

The following Table 5 reports the results.

TABLE 5

| | LDH release in perfusate (mL/ml/min) | | |
|---|---|---|---|
| | Control | ST1364 1 μM * | ST1364 5 μM ** |
| Basal | 280 | 275 | 220 |
| Ischemia 30' | 200 | 220 | 200 |
| Reperfusion 1' | 640 | 480 | 410 |
| Reperfusion 5' | 660 | 500 | 380 |
| Reperfusion 10' | 670 | 495 | 380 |
| Reperfusion 15' | 700 | 510 | 320 |
| Reperfusion 20' | 720 | 580 | 325 |

Statistical analysis was carried out with Student's "t" test for non-paired data. * $p<0.05$ vs controls; ** $p<0.01$ vs controls.

The number of the cases for each group is six (n=6).

LDH release in the effluent is remarkably reduced, during reperfusion results significantly reduced in the presence of ST1364 at the dose of 5 μM (FIG. 1). This result indicates a lower entity of cellular damage from reperfusion of the treated with respect to the controls.

In another aspect, the present invention provides a combination of at least a compound of formula (I) with at least another active ingredient suitable for the treatment of the disease of interest.

In the treatment or prevention of diabetes, the present invention provides a compound of formula (I), optionally in combination with a suitable well-known active ingredient, such as for example a sulfonylurea, L-carnitine, fibrate and other agonists of peroxisomal proliferator activated receptor (PPAR-α), agonists of 9-cis retinoic acid activated receptor, such as RXR, in particular α-,β- and γ-isoforms, HMGCoA reductase inhibitor, β-sitosterol inhibitor, cholesterol acyltransferase inhibitor, biguanides, cholestyramine, angiotension II antagonist, melinamide, micotinic acid, fibrinogen receptor antagonists, aspirin, α-glucosidase inhibitors, insulin secretogogue, insulin and glucagon-like peptides (incretins) and agonists of PPAR-γ (such as thiazolidinediones or others).

In the treatment or prevention of obesity, the present invention provides a compound of formula (I), optionally in combination with an suitable well-known active ingredient, such as for example fenfluramine, dexfenfluramine, phentiramine, a β-3-adrenergic receptor agonist.

In the treatment or prevention of high triglyceridhemia, the present invention provides a compound of formula (I), optionally in combination with an suitable well-known active ingredient.

The compounds according to the present invention are also useful in the treatment or prevention of high cholesterol levels and in modulating HDL plasma levels, thus resulting beneficial in the treatment or prevention of the diseases related with these altered plasma levels. Examples of related diseases are hypertension, obesity, atherosclerosis, diabetes and related conditions. The medicaments containing at least a compound of the present invention may contain in combination at least another active ingredient effective in the treatment or prevention of the above mentioned diseases. Examples of other active ingredient are fibrates, such as clofibrate, bezafibrate and gemfibrozil and other PPAR-α agonists; inhibitors of cholesterol biosynthesis, such as HMG-CoA reductase inhibitors, such as statins, namely lovastatin, simvastatin and pravastatin; inhibitors of cholesterol absorption for example beta-sitosterol and (acyl CoA: cholesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; thyromimetics and L-carnitine.

The compounds of the present invention may be orally administered in the form of a pharmaceutical composition, comprising a therapeutically effective amount of at least a compound of formula (I) in admixture with a pharmaceutically acceptable vehicle and/or excipient. Examples of oral pharmaceutical compositions are hard or soft capsules, tablets, including sublingual administration, ampoules, sachets, elixirs, suspensions, syrups, and the like. Alternatively, the active ingredients according to the present invention may be incorporated directly with the food of the diet. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in pyrogen-free water.

The pharmaceutical forms suitable for injectable use include sterile aqueous solutions or dispersions and sterile powders for the extemporaneous preparation of sterile injectable solutions or dispersions.

If desired, or deemed necessary, the pharmaceutical compositions may be in the controlled- release form. Various techniques for preparing these forms are known.

General reference for pharmaceutical compositions can be made to "Remington's Pharmaceutical Sciences Handbook", Mack Pub. N.Y. USA.

The effective dosage of active ingredient employed may vary depending on the particular compound employed, the mode of administration, the condition being treated and the severity of the condition being treated.

The compositions are formulated and administered in the same general manner as detailed below. The compounds of the present invention can be used effectively alone or in combination with one or more additional active agents depending on the desired target therapy. Combination therapy includes administration of a single pharmaceutical dosage formulation which contains a compound of formula I and one or more additional active agents, as well as administration of a compound of formula I and each active agent in its own separate pharmaceutical dosage formulation. For example, a compound of formula I and an HMG-CoA reductase inhibitor can be administered to the patient together in a single oral dosage composition such as a tablet or capsule, or each agent administered in separate oral dosage formulations. Where separate dosage formulations are used, a compound of formula I and one or more additional active agents can be administered at essentially the same time, i.e., concurrently, or sequentially; combination therapy is understood to include all these regimens.

An example of combination treatment or prevention of atherosclerosis is wherein a compound of formula I is administered in combination with one or more of the following active agents: an antihyperlipidemic agent; a plasma HDL-raising agent; an antihypercholesterolemic agent such as a cholesterol biosynthesis inhibitor, for example an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A: cholesterol acyltransferase (ACAT) inhibitor such as melinamide; probucol; nicotinic acid and the salts thereof and niacinamide; a cholesterol absorption inhibitor such as beta-sitosterol; a bile acid sequestrant anion exchange resin such as cholestyramine, colestipol or dialkylaminoalkyl derivatives of a cross-linked dextran; an LDL (low density lipoprotein) receptor inducer; fibrates such as clofibrate, bezafibrate, fenofibrate, and gemfibrozil and other PPAR-α agonists, L-carnitine; vitamin $B_6$ and the pharmaceutically acceptable salts thereof; vitamin $B_{12}$; anti-oxidant vitamins such as vitamin C and E and beta carotene; a beta-blocker; an angiotensin II antagonist; an angiotensin converting enzyme inhibitor; and a platelet aggregation inhibitor such as fibrinogen receptor antagonists (i.e., glycoprotein IIb/IIIa fibrinogen receptor antagonists) and aspirin. The compounds of formula I can be administered in combination with more than one additional active agent.

Another example of combination therapy can be seen in treating obesity or obesity-related disorders, wherein-the compounds of formula I may be effectively used in combination with for example, fenfluramine, dexfenfluramine, phentiramine and β-3 adrenergic receptor agonists agents and L-carnitine.

Another example of combination therapy can be seen in treating diabetes and related disorders wherein the compounds of formula I can be effectively used in combination with for example sulfonylureas, biguanides, α-glucosidase inhibitors, other insulin secretogogues, insulin and glucagon-like peptides (incretins) and agonists of PPAR-γ (such as thiazolidinediones or others) as well as the active agents discussed above for treating atherosclerosis.

What is claimed is:

1. A compound of formula (I)

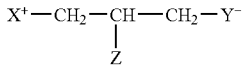

wherein: $X^+$ is $N^+(R_1,R_2,R_3)$, wherein $R_1,R_2,R_3$, being the same or different, are selected in the group consisting of hydrogen, a $C_1$–$C_9$ straight or branched alkyl group, —CH═NH($NH_2$), —$NH_2$, and —OH; or one or more $R_1$, $R_2$ and $R_3$, together with the nitrogen atom which they are linked to, form a saturated or unsaturated, monocyclic or bicyclic heterocyclic system; with the proviso that at least one of the $R_1$, $R_2$ and $R_3$ is different from hydrogen;

Z is selected from

[—$OR_4$,]

—$OCOOR_4$,

—$OCONHR_4$,

—$OCSNHR_4$,

—$OCSOR_4$,

[—$NHR_4$,]

[—$NHCOR_4$,]

—$NHCSR_4$,

—$NHCOOR_4$,

—$NHCSOR_4$,

—$NHCONHR_4$,

—$NHCSNHR_4$,

—$NHSOR_4$,

—$NHSONHR_4$,

—$NHSO_2R_4$,

—$NHSO_2NHR_4$, and

—$SR_4$, wherein —$R_4$ is a [$C_1$–$C_{20}$ saturated or unsaturated,] straight or branched alkyl group, [optionally] *selected from the group consisting of ethyl, propyl, butyl, pentyl, hexyl, heptyl, octal, nonyl, decyl, undecyl, dodecyl, tridecyl, tetradecyl, pentadecyl, hexadecyl, heptadecyl, octadecyl, nonadecyl and eicosyl and their possible isomers or a linear or branched alkenyl group selected from the group consisting of ethylidene, vinyl, allyl, propenyl, butenyl, pentenyl, and their possible isomers, wherein said alkyl or alkenyl group is* substituted with an $A_1$ group, wherein $A_1$ is selected from the group consisting of a halogen atom, or an aryl, heteroaryl, aryloxy or heteroaryloxy group, said aryl, heteroaryl, aryloxy or heteroaryloxy groups being optionally substituted with one or more $C_1$–$C_{20}$ saturated or unsaturated, straight or branched alkyl or alkoxy group and/or halogen atom;

$Y^-$ is selected from the group consisting of —$COO^-$, $PO_3H^-$, —$OPO_3H^-$, tetrazolate-5-yl;

[with the proviso that when Z is —$NHCOR_4$, Y is —$COO^-$, then $R_4$ is $C_{20}$ alkyl;]

with the proviso that when Z is —$NHSO_2R_4$, $Y^-$ is —$COO^-$, then $R_4$ is not tolyl;

[with the proviso that when Z is —$NHR_4$, $X^+$ is trimethylammonium and $Y^-$ is —$COO^-$, then $R_4$ is not $C_1$–$C_6$ alkyl,]

their (R,S) racemic mixtures, their single R or S enantiomers, or their pharmaceutically acceptable salts.

2. A compounds according to claim 1, wherein $R_1$, $R_2$ and $R_3$ are methyl.

3. A compounds according to claim 1, wherein the heterocyclic system formed by $R_1$, $R_2$ and $R_3$ together with nitrogen is selected from the group consisting of morpholinium, quinuclidinium, pyridinium, quinolinium and pyrrolidinium.

4. A compound according to claim 1, wherein $R_1$ and $R_2$ are H, $R_3$ is selected from the group consisting of —CH═NH($NH_2$), —$NH_2$ and —OH.

5. A compound [according to claim 1, wherein] *of formula 1*

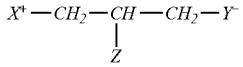

*wherein: X+ is $N^+(R_1,R_2,R_3)$, wherein $R_1$, $R_2$, $R_3$, being the same or different, are selected in the group consisting of hydrogen, a $C_1$–$C_9$ straight or branched alkyl group, —CH═NH($NH_2$), —$NH_2$ and —OH; or one or more $R_1$, $R_2$ and $R_3$, together with the nitrogen atom which they are linked to, form a saturated or unsaturated, monocyclic or bicyclic heterocyclic system; with the proviso that at least one of the $R_1$, $R_2$ and $R_3$, is different from hydrogen; and*

Z is selected from the group consisting of ureido (—$NHCONHR_4$) or carbamate (—$OCONHR_4$), and $R_4$ is a $C_7$–$C_{20}$ saturated or unsaturated, straight or branched alkyl group.

6. A compound according to claim 5, wherein $R_4$ is a $C_9$–$C_{18}$ saturated or unsaturated, straight or branched alkyl group.

7. A compound selected from the group consisting of

R,S-4-trimethylammonium-3-(nonylcarbamoyl)-aminobutyrate;

R,S-4-quinuclidinium-3-(tetradecyloxycarbonyl)-oxybutyrate;

R,S-4-trimethylammonium-3-(nonylcarbamoyl)-oxybutyrate;

R,S-4-trimethylammonium-3-(nonyloxycarbonyl)-oxybutyric acid chloride;

[R,S-4-trimethylphosphonium-3-(nonylcarbamoyl)-oxybutyrate;]

R,S-4-trimethylammonium-3-(nonyloxycarbonyl)-aminobutyrate;

R,S-4-trimethylammonium-3-(octyloxycarbonyl)-aminobutyrate;

[R,S-4-trimethylammonium-3-(nonyloxycarbonyl)-aminobutyrate;]

[R,S-4-trimethylammonium-3-octyloxybutyrate;

R,S-4-trimethylammonium-3-tetradecyloxybutyrate;

R,S-1-guanidinium-2-tetradecyloxy-3-(tetrazolate-5-yl)-propane;

R,S-4-trimethylammonium-2-tetradecyloxy-3-(tetrazolate-5-yl)-propane;]

R,S-3-quinuclidinium-2-(tetradecyloxycarbonyl)-oxy-1-propanephosphonate monobasic;

R,S-3-trimethylammonium-2-(nonylaminocarbonyl)-oxy-1-propanephosphonate monobasic;

R,S-3-pyridinium-2-(nonylaminocarbonyl)-oxy-1-propanephosphonic acid chloride;

R-4-trimethylammonium-3-(tetradecylcarbamoyl)-aminobutyrate;

R-4-trimethylammonium-3-(undecylcarbamoyl)-aminobutyrate;

R-4-trimethylammonium-3-(heptylcarbamoyl)-aminobutyrate;

R,S-4-trimethylammonium-3-(nonylthiocarbamoyl)-aminobutyrate;

R-4-trimethylammonium-3-(nonylcarbamoyl)-aminobutyrate;

S-4-trimethylammonium-3-(nonylcarbamoyl)-aminobutyrate;

S-4-trimethylammonium-3-(tetradecylcarbamoyl)-aminobutyrate;

[R,S-4-trimethylammonium-3-tetradecylaminobutyrate;]

[R,S-4-trimethylammonium-3-octylaminobutyrate;]

R,S-4-trimethylammonium-3-(decansulfonyl) aminobutyrate;

R,S-4-trimethylammonium-3-(nonylsulfamoyl) aminobutyrate;

S-4-trimethylammonium-3-(dodecansulfonyl) aminobutyrate;

R-4-trimethylammonium-3-(dodecansulfonyl) aminobutyrate;

S-4-trimethylammonium-3-(undecylsulfamoyl) aminobutyrate;

R-4-trimethylammonium-3-(undecylsulfamoyl) aminobutyrate;

R-4-trimethylammonium-3-(dodecylcarbamoyl) aminobutyrate;

R-4-trimethylammonium-3-(10-phenoxydecylcarbamoyl)aminobutyrate; and

R-4-trimethylammonium-3-(trans-β-styrenesulfonyl) aminobutyrate.

8. A process for the preparation of a compound of claim 1, wherein Z is carbonate (—$OCOOR_4$), carbamate (—$NHCOOR_4$), thiocarbamate (—$OCSNHR_4$) or thiocarbonate (—$OCSOR_4$), said process comprising reacting X+—$CH_2$—CH(OH)—$CH_2$—Y—, of the desired structure, optionally protected on the acid Y— group, respectively with an alkyl chloroformate, alkyl isocyanate, alkyl isothiocyanate or alkyl thiochloroformate, wherein the alkyl moiety is the desired $R_4$ alkyl group, to produce the desired compound.

9. A process for a preparation of a compound of claim 1, wherein Z is [amide (—$NHCOR_4$),] thioamide (—$NHCSR_4$), carbamate (—$NHCOOR_4$), thiocarbamate (—$NHCSOR_4$), ureido (—$NHCONHR_4$), thioureido (—$NHCSNHR_4$), sulfinamide (—$NHSOR_4$), sulfonamide (—$NHSO_2R_4$), sulfinamoylamino (—$NHSONHR_4$), and sulfamide (—$NHSO_2NHR_4$), said process comprising reacting $X^+$—$CH_2$—CH(OH)—$CH_2$—$Y^-$, of the desired structure, optionally protected on the acid $Y^-$ group, respectively with an acyl chloride, thioacyl chloride, alkyl chloroformate, alkyl thiochloroformate, alkyl isocyanate, alkyl thioisocyanate, alkyl sulfinyl chlorides, alkyl sulfonyl chlorides, $SOCl_2$ and alkyl amines, alkyl sulfamoyl chloride or $SOCl_2$ and alkyl amine, wherein the alkyl moiety is the desired $R_4$ alkyl group, to produce the desired compound.

10. A process for the preparation of a compound of claim 1, wherein Z is [—$OR_4$ or] —$SR_4$, said process comprising the steps of:

(a) reacting a carbonyl compound of formula Hal-$CH_2$—CO—$CH_2$—COOR', wherein Hal is a halogen atom and R' is the residue of a suitable ester, with [respectively alcohols and] thiols [$R_4OH$ or] $R_4SH$, to give the respective [ketal or] thioketal;

(b) transforming the respective [ketal or] thioketal into the respective [ether or] thioether;

(c) substituting the Hal atom with an azido group, and (d) transforming the azido group into the X+ group to produce the desired compound.

[11. A process for the preparation of a compound of claim 1, wherein Z is —$NHR_4$, said process comprising reacting of $X^+$—$CH_2$—CH($NH_2$)—$CH_2$—$Y^-$ of the desired structure, optionally protected on the acid $Y^-$ group, with alkane carbaldheydes, wherein the alkyl moiety is a one-term lower homologue of the desired $R_4$, and subsequent reduction, to produce the desired compound.]

12. A pharmaceutical composition comprising a therapeutically effective amount of a compound of claim 1, in admixture with a pharmaceutically acceptable vehicle or and excipient.

13. The pharmaceutical composition according to claim 12, wherein [an active ingredient suitable] *a biguanide* for the treatment of diabetes is also present [and is selected from the group consisting of sulfonylurea, L-carnitine, fibrate and other agonists of peroxisomal proliferator activated receptor (PPAR-α), HMG-CoA reductase inhibitor, β-sitosterol inhibitor, cholesterol acyltransferase inhibitor, biguanides, cholestyramine, angiotensin II antagonist, melinamide, nicotinic acid, fibrinogen receptor antagonists, aspirin, α-glucosidase inhibitors, insulin secretogogue, insulin and glucagon-like peptides and agonists of PPAR-γ].

[14. A pharmaceutical composition according to claim 12, also including an active ingredient suitable for the treatment of obesity selected from the group consisting of fenfluramine, dexfenfluramine, phentiramine, and a β-3-adrenergic receptor agonist.]

[15. A pharmaceutical composition according to claim 12, also including an active ingredient suitable for the treatment of high cholesterol levels and in modulating HDL plasma levels, which is selected from the group consisting of fibrates, and other PPAR-α agonists; inhibitors of cholesterol biosynthesis, HMG-CoA reductase inhibitors, statins, inhibitors of cholesterol absorption, acyl CoA:cholesterol acyltransferase inhibitors, anion exchange resins, nicotinyl alcohol, nicotinic acid or a salt thereof, vitamin E, thyromimetics and L-carnitine.]

16. A method for treating *obesity in* a subject [having hyperactive] *and inhibiting* carnitine palmitoyl-transferase *in the subject* comprising administering to said subject an effective amount of a compound of claim 1.

17. A method for treating [a subject having] hyperglycaemia, diabetes[, heart failure] or ischemia *in a subject* comprising administering to said subject an effective amount of a compound of claim 1.

[18. A method for treating a subject having obesity comprising administering to said subject an effective amount of a compound of claim 1.]

[19. A method for treating a subject having high triglyceridemia comprising administering to said subject an effective amount of a compound of claim 1.]

[20. A method for treating a subject having hypertension comprising administering to said subject an effective amount of a compound of claim 1.]

[21. A method of modulating high cholesterol levels or MDL plasma levels in a subject in need of same, said method comprising administering to said subject an effective amount of a compound of claim 1.]

* * * * *